US007960430B2

(12) United States Patent
Wirth et al.

(10) Patent No.: US 7,960,430 B2
(45) Date of Patent: Jun. 14, 2011

(54) FLAVONOID COMPLEXES WITH CYCLODEXTRINS

(75) Inventors: Corinna Wirth, Darmstadt (DE); Ralf Rosskopf, Muenster (DE); Herwig Buchholz, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 470 days.

(21) Appl. No.: 10/586,458

(22) PCT Filed: Dec. 27, 2004

(86) PCT No.: PCT/EP2004/014729
§ 371 (c)(1),
(2), (4) Date: Jul. 18, 2006

(87) PCT Pub. No.: WO2005/068484
PCT Pub. Date: Jul. 28, 2005

(65) Prior Publication Data
US 2007/0155695 A1 Jul. 5, 2007

(30) Foreign Application Priority Data
Jan. 19, 2004 (DE) .......................... 10 2004 002 787

(51) Int. Cl.
*A61K 31/353* (2006.01)
(52) U.S. Cl. ........ 514/427; 514/456; 514/861; 514/887; 424/59; 424/70.1; 424/401
(58) Field of Classification Search .................. None
See application file for complete search history.

(56) References Cited

U.S. PATENT DOCUMENTS

| 5,472,954 A * | 12/1995 | Loftsson ................ 514/58 |
| 2003/0105031 A1 * | 6/2003 | Rosenbloom .......... 514/27 |
| 2004/0081675 A1 | 4/2004 | Wirth et al. |
| 2007/0020350 A1 * | 1/2007 | Numano et al. ....... 424/769 |

FOREIGN PATENT DOCUMENTS

| EP | 0 796 624 A | | 9/1997 |
| JP | 59-137 499 | | 8/1984 |
| JP | 2-268643 | | 11/1990 |
| JP | 05-186 344 | | 7/1993 |
| JP | 07-075 536 | | 3/1995 |
| WO | WO 02/069926 | * | 9/2002 |
| WO | WO 02/069926 A | | 9/2002 |

OTHER PUBLICATIONS

Sala et al. Assessment of the anti-inflammatory activity and free radical scavenger activity of tiliroside, European Journal of Pharmacology, 461, 53-61, 2003.*
Christoff et al. Dynamics of Complexation of flavone and chromone to B-cyclodextrin, Journal of Photochemistry and Photobiology A: Chemistry 134, 169-176, 2000.*
Buschmann et al. Applications of cyclodextrins in cosmetic products: A review, Journal of Cosmetic Science, 53, 185-191, 2002.*

Hostettmann et al. A Study of the Cyclodextrin Complexes of Flavonoids and Azodyes by Thin Layer Chromatography. Part II. Hydroxyproply-cyclodextrins, Phytochemical Analysis, 11, 380-382, 2000.*
Miyake et al. Improvement of Solubility and Oral Bioavailability of Rutin by Complexation with 2-Hydroxypropyl-B-cyclodextrin, Pharmaceutical Development and Technology, 5(3), 399-407, 2000.*
Ficarra et al. Study of Flavonoids/B-cyclodextrins inclusion complexes by NMR, FT-IR, DSC, X-ray investigation, Journal of Pharmaceutical and Biomedical Analysis, 29, 1005-1014, 2002.*
Wollenberg et al., Tropical Immunomodulatory Agents and Their Targets in Inflammatory Skin Diseases, Transplantation Proceedings 2001, pp. 2212-2216.*

(Continued)

*Primary Examiner* — Neil Levy
(74) *Attorney, Agent, or Firm* — Millen, White, Zelano & Branigan, P.C.

(57) ABSTRACT

The invention relates to complexes of certain flavonoid derivatives, of the formula I compositions which comprise such derivatives, corresponding processes for the preparation of the flavonoid derivatives or of compositions comprising same, and the use thereof, in particular for the care, preservation or improvement of the general state of the skin or hair. Formula (1), in which $Z_1$ to $Z_4$ and $Z_6$ to $Z_{10}$ each, independently of one another, denote H, OH, $CH_3COO$, alkoxy, hydroxyalkoxy, mono- or oligoglycoside radicals and where the alkoxy and hydroxyalkoxy groups may be branched and unbranched and can have 1 to 18 C atoms. Formula (II) denotes, $Z_5$ is a mono- or the oligoglycoside radical, where bonded to this glycoside radical, in each case via an —O— group, is at least one radical selected from certain benzo molecule.

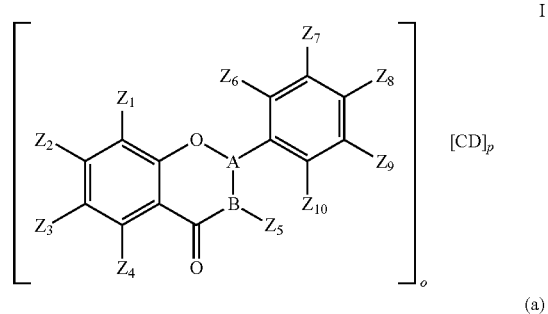

(a)

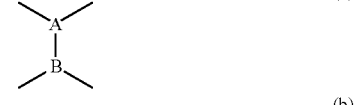

(b)

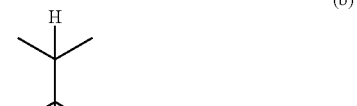

(c)

13 Claims, No Drawings

OTHER PUBLICATIONS

Buschmann H-J et al: "Applications of Cyclodextrins in Cosmetic Products: A Review" Journal of Cosmetic Science, Society of Cosmetic Chemists, New York, NY, US, Bd. 53, Nr. 3, May 2002, pp. 185-191, XP008013888; ISSN: 1525-7886.

Loftsson T et al: "Cylodextrins in Topical Drug Formulations: Theory and Practice" Internaional Journal of Pharmaceutics, Amsterdam, NL., Bd. 225, Nr. 1/2, Aug. 2001; pp. 15-30, XP001023910; ISSN: 0378-5173.

K. Miyake, et al.: "Improvement of Solubility and Oral Bioavailability of Rutin by Complexation With 2-Hydroxypropyl-β-Cyclodextrin" Pharmaceutical Development and Technology, 5(3), pp. 399-407 (2000).

Nguyen, et al.: "Study of Inclusion Compounds of Rutin" Congr. in. Technol. Pharm., 6$^{th}$ (1992), vol. 5, pp. 408-416.

Dimova, et al.: "Safety-Assessment of 3-Methoxyquercetin as an Antirhinoviral Compound for Nasal Application: Effect on Ciliary Beat Frequency", Int. J. Pharm. 263 (2003), pp. 95-103.

Ficarra, et al.: "Study of Flavonoids/β-Cyclodextrins Inclusion Complexes by NMR, FT-IR, DSC, X-Ray Investigation", J. Pharm. Biomed. Analysis 29 (2002), pp. 1005-1014.

Wang, et al.: "Enhanced Solubility of Flavonoids by Inclusion With β-Cyclodextrin and its Derivatives", Chin. J. Applied Chem., vol. 19, (2002), pp. 702-704.

Hostettmann, et al.: "A Study of the Cyclodextrin Complexes of Flavonoids and AZO-Dyes by Thin Layer Chromatography. Part II. Hydroxypropylcyclodextrins", Phytochemical Analysis, vol. 11, pp. 380-382 (2000).

* cited by examiner

FLAVONOID COMPLEXES WITH CYCLODEXTRINS

The invention relates to complexes of certain flavonoid derivatives, to compositions which comprise such derivatives, to corresponding processes for the preparation of the flavonoid derivatives or the compositions comprising same, and to the use thereof, in particular for the care, preservation or improvement of the general state of the skin or hair.

International patent application WO 02/69926 describes compounds

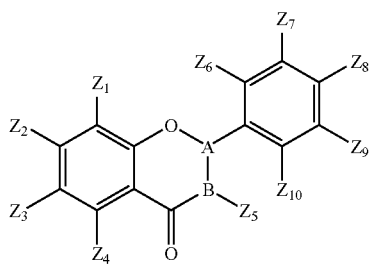

in which $Z_1$ to $Z_4$ and $Z_6$ to $Z_{10}$ each, independently of one another, denote H, OH, $CH_3COO$, alkoxy, hydroxyalkoxy, mono- or oligoglycoside radicals and where the alkoxy and hydroxyalkoxy groups may be branched and unbranched and can have 1 to 18 C atoms,

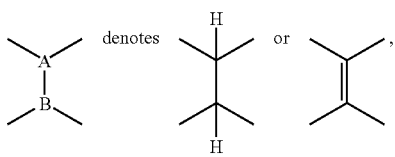

$Z_5$ is a mono- or oligoglycoside radical, where bonded to this glycoside radical, in each case via an —O— group, is at least one radical selected from

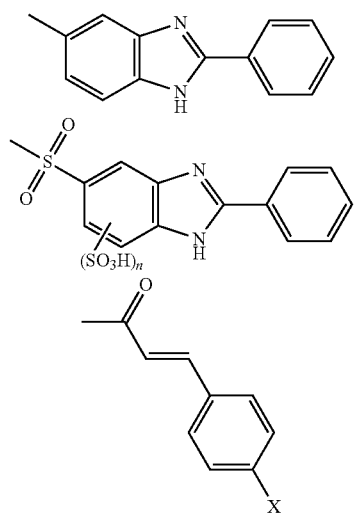

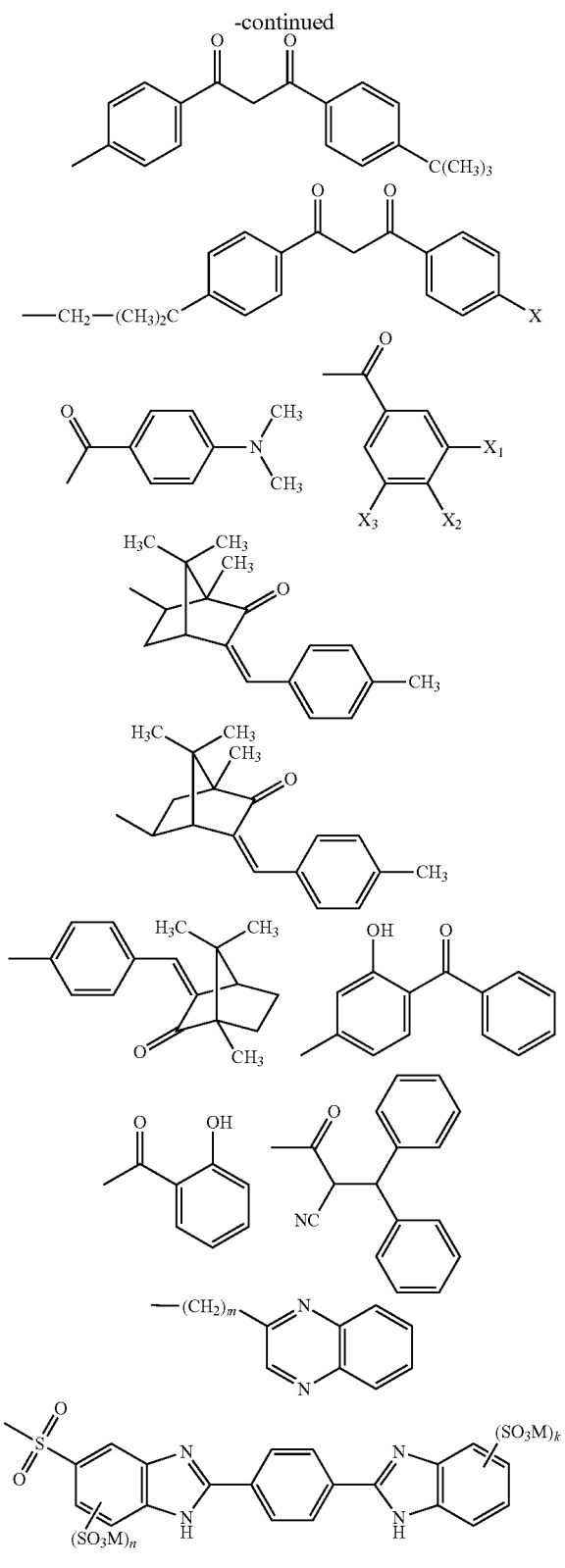

in which X, $X_1$, $X_2$ and $X_3$ each, independently of one another, denote OH, $CH_3COO$, an alkoxy radical having 1 to 8 C atoms or a monoglycoside radical, n is 0, 1, 2 or 3, m is 0 or 1, k is 0, 1, 2, 3 or 4 and M is H, Na or K, and in which one or more hydrogen atoms in the OH groups of the glycoside radicals mentioned in the substituents $Z_1$ to $Z_{10}$ may each, independently of one another, also be replaced by acetyl or alkyl radicals and where sulfate or phosphate may also each, independently of one another, be bonded to one or more hydroxyl groups of the radicals mentioned in the substituents $Z_1$ to $Z_{10}$. These compounds are suitable for use in cosmetic and pharmaceutical compositions. In particular, WO 02/69926 describes the suitability of these compounds for use as UV filters and the use as active ingredient for protection against oxidative stress and for preventing skin ageing. It is furthermore described that these compounds exhibit antiallergic, antiinflammatory, inflammation-inhibiting and antiirritative properties and can thus be used for the treatment or preventive treatment of allergies, inflammation and irritation, in particular of the skin. Particularly preferred representatives here are kaempferol-3-(6"-galloylglucoside) and kaempferol-3-(6"-p-coumarylglucoside), which is also referred to as tiliroside.

DE 195 44 905 A1 describes, for example, a process for the preparation of plant extracts comprising tiliroside and the use of the plant extracts in medicaments and food products.

DE 199 22 287 A1 describes tiliroside as a starting flavonoid for the preparation of tiliroside esters whose acid unit contains 3 to 30 C atoms. These esters are used in cosmetics. However, DE 199 22 287 A1 does not describe any compositions comprising tiliroside.

The earlier European patent application with the application file reference EP 03015616.0 describes the suitability of these compounds for the treatment of eczema. The compounds here are particularly advantageous in the treatment of atopic eczema, such as, in particular, milk crust, neurodermatitis, prurigo and dermatitis sicca. The compounds here are able greatly to reduce the acute symptoms, reduce the frequency of occurrence of acute symptoms and in general contribute to an improvement in the skin picture.

On use of these compounds, there is a wish for administration forms which can be incorporated more easily into compositions, whose compositions exhibit increased storage stability, or in which the bioavailability of the compounds is increased.

Surprisingly, it has now been found that the complexing of these compounds with cyclodextrins results in products which meet the said requirements in an excellent manner.

The present invention therefore relates firstly to complex compounds of the formula I

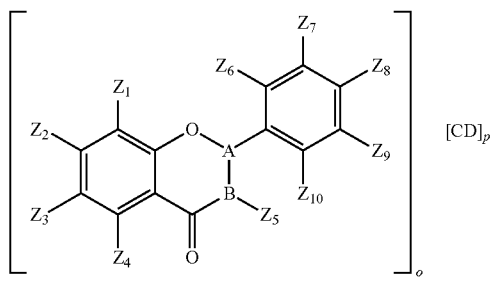

in which
$Z_1$ to $Z_4$ and
$Z_6$ to $Z_{10}$ each, independently of one another, denote H, OH, $CH_3COO$, alkoxy, hydroxyalkoxy, mono- or oligoglycoside radicals and where the alkoxy and hydroxyalkoxy groups may be branched and unbranched and can have 1 to 18 C atoms,

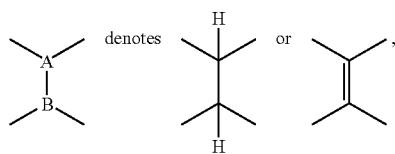

$Z_5$ is a mono- or oligoglycoside radical, where bonded to this glycoside radical, in each case via an —O— group, is at least one radical selected from

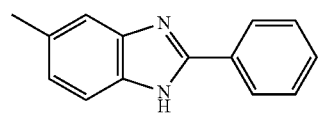

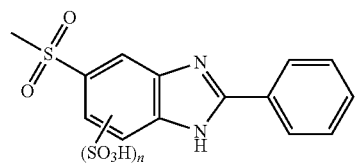

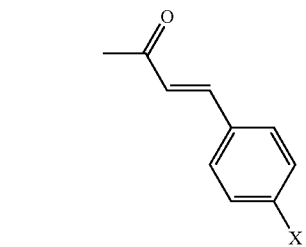

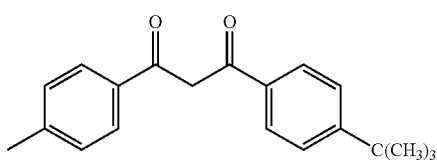

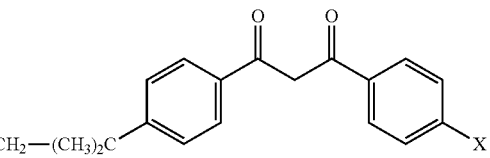

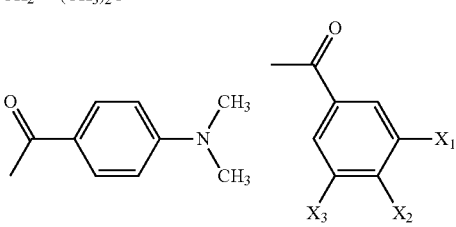

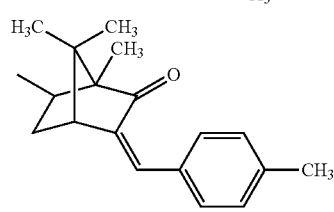

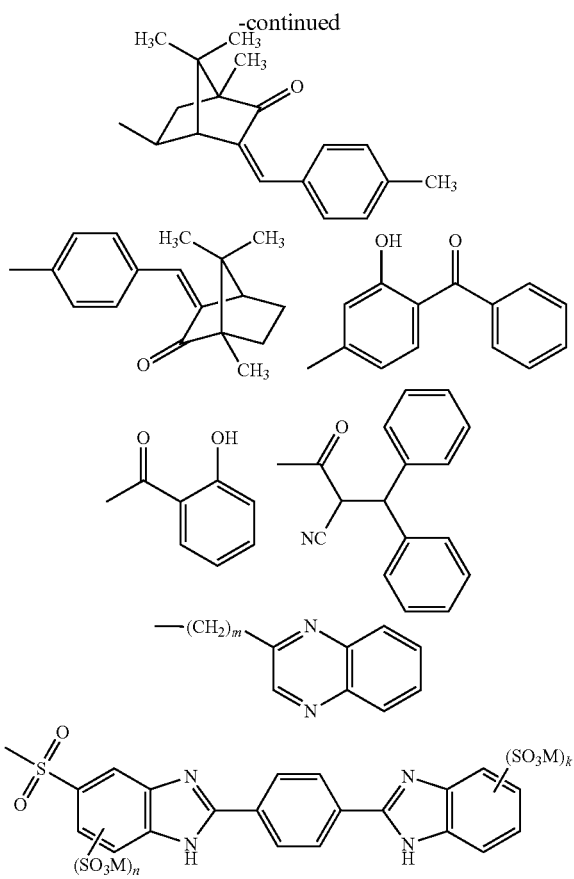

in which

X, $X_1$, $X_2$ and $X_3$ each, independently of one another, denote OH, $CH_3COO$, an alkoxy radical having 1 to 8 C atoms or a monoglycoside radical, n is 0, 1, 2 or 3, m is 0 or 1, k is 0, 1, 2, 3 or 4 and M is H, Na or K, and CD stands for a cyclodextrin molecule o stands for the number 1 und p stands for a number from the range 0.5 to 3, where one or more hydrogen atoms in the OH groups of the glycoside radicals mentioned in the substituents $Z_1$ to $Z_{10}$ may each, independently of one another, also be replaced by acetyl or $C_{1-24}$-alkyl radicals and where sulfate or phosphate may also each, independently of one another, be bonded to one or more hydroxyl groups of the radicals mentioned in the substituents $Z_1$ to $Z_{10}$.

The present application relates secondly to compositions comprising a suitable excipient, characterised in that the compositions comprises 0.005 to 99% by weight of a complex compound of the formula I according to claim 1 or the composition comprises 0.002 to 70% by weight of cyclodextrin and 0.001 to 60% by weight of at least one compound of the formula II or topically tolerated salts and/or derivatives thereof,

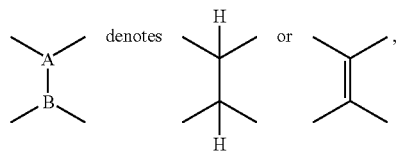

in which $Z_1$ to $Z_4$ and $Z_6$ to $Z_{10}$ each, independently of one another, denote H, OH, $CH_3COO$, alkoxy, hydroxyalkoxy, mono- or oligoglycoside radicals and where the alkoxy and hydroxyalkoxy groups may be branched and unbranched and can have 1 to 18 C atoms,

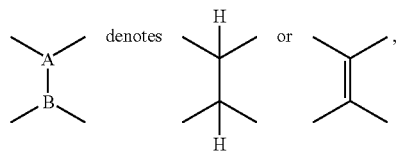

$Z_5$ is a mono- or oligoglycoside radical, where bonded to this glycoside radical, in each case via an —O— group, is at least one radical selected from

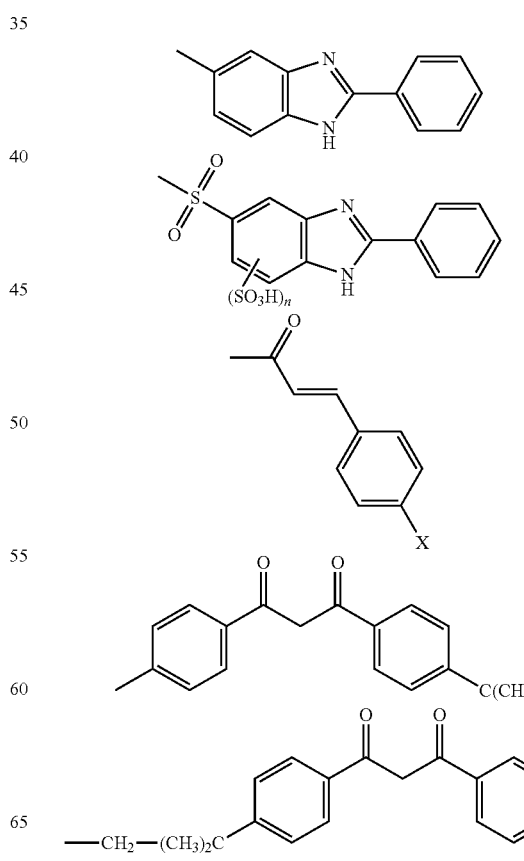

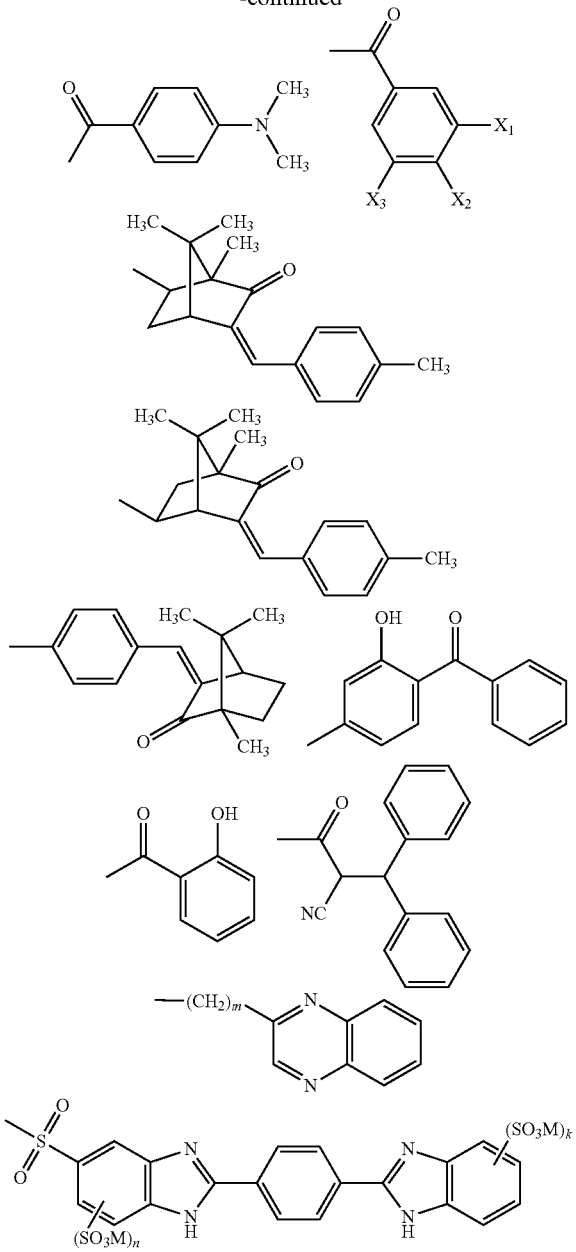

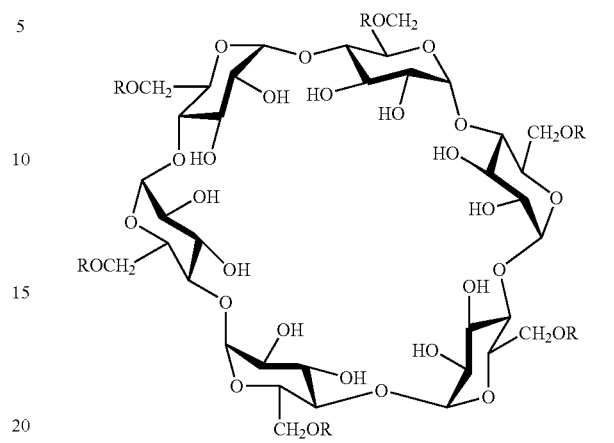

Cyclodextrins are built up from 6, 7, 8 or even more α-1,4-linked glucose units, with cycloohexaamylose (alpha- or α-cyclodextrin) being distinguished by the structure Cycloheptaamylose (beta- or β where bonded to this glycoside radical, in each case via an —O— group, is at least one radical selected from β-cyclodextrin) is distinguished by the structure

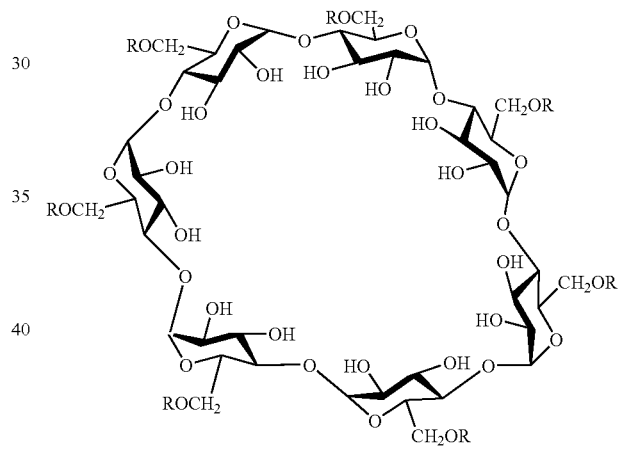

Cyclooctaamylose (gamma- or γ-cyclodextrin) is distinguished by the structure

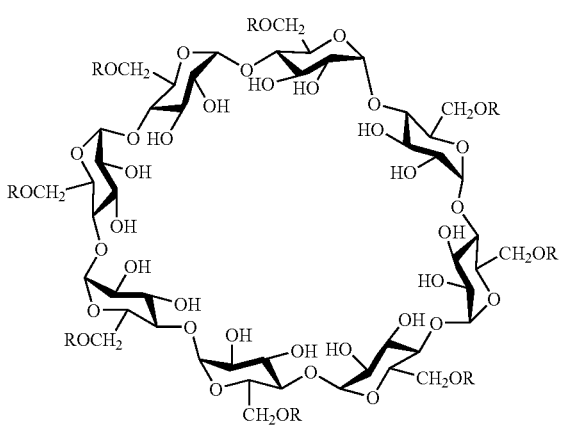

in which X, $X_1$, $X_2$ and $X_3$ each, independently of one another, denote OH, $CH_3COO$, an alkoxy radical having 1 to 8 C atoms or a monoglycoside radical, n is 0, 1, 2 or 3, m is 0 or 1, k is 0, 1, 2, 3 or 4 and M is H, Na or K, and in which one or more hydrogen atoms in the OH groups of the glycoside radicals mentioned in the substituents $Z_1$ to $Z_{10}$ may each, independently of one another, also be replaced by acetyl or $C_{1-24}$-alkyl radicals and where sulfate or phosphate may also each, independently of one another, be bonded to one or more hydroxyl groups of the radicals mentioned in the substituents $Z_1$ to $Z_{10}$.

The compositions according to the invention here are usually either compositions which can be used topically, for example cosmetic or dermatological formulations, or medicaments or foods or food supplements. The compositions comprise a cosmetically or dermatologically or pharmaceutically or food-suitable excipient and, depending on the desired property profile, optionally further suitable ingredients.

Cycloenneaamylose (delta- or δ-cyclodextrin) is distinguished by the structure

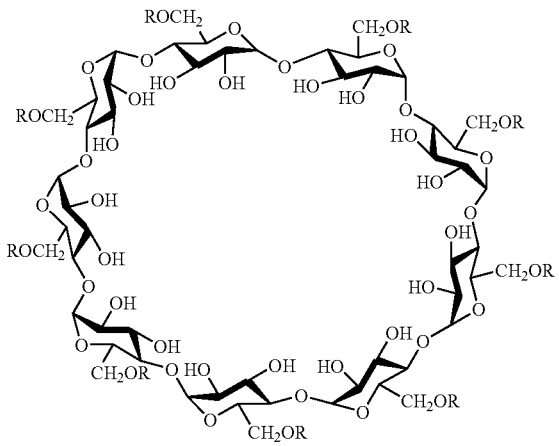

Cyclodextrins may occur in underivatised form (R=H) or also in derivatised form, for example alkoxylated, hydroxyalkylated or alkylated, in particular propoxylated or methylated, in position R.

Bioflavonoid/cyclodextrin complexes here are known in principle:

K. Miyake, H. Arima et al. (Pharm. Dev. Techn. 5(3) 2000, 399-407 describe 1:1 complexes of rutin with beta-cyclodextrins and the solubility and liberation behaviour thereof. It was found here that the beta-cyclodextrin complex and the 2-hydroxypropyl-beta-cyclodextrin complex are particularly stable. Alpha- and gamma-cyclodextrin complexes are, according to this publication, generally less suitable for complexing rutin than are beta-cyclodextrin complexes.

T. K. Nguyen, H. Galons, C. Chemtob, Congr. Int. Technol. Pharm., 6th (1992), Vol 5, 408-16408-416 likewise describe various cyclodextrin complexes of rutin. The 2,6-di-O-methyl-beta-cyclodextrin complex proves to be particularly soluble here, with complexes having rutin:cyclodextrin molar ratios of 1:1 and 1:2 being described.

Complexes of isoflavones in soya beans or fermented soya beans with beta- and gamma-cyclodextrins are described in European Patent Application EP-A-796 624. The complexing increases the solubility of isoflavones and reduces their bitterness.

Rutin complexes with beta- and gamma-cyclodextrins and the use thereof as antioxidant are described in Japanese Patent Application JP 05/9137499.

Beverages comprising cyclodextrin complexes of quercetin glycosides are described in Japanese Patent Application JP 07/075,536.

Japanese Patent Application JP 05/186344 describes compositions comprising vitamin C and cyclodextrin complexes of vitamin P which improve the bioabsorption of vitamin C. Complexes of rutin, hesperidin and eriocitrin, such as, for example, a rutin/beta-cyclodextrin complex having a molar ratio of 1.2, are described.

The action of a complex of 3-methoxyquercetin with hydroxypropyl-beta-cyclodextrin on nasal epithelial cells is investigated in S. Dimova, R. Mugabowindekwe et al. Int. J. Pharm. 26381-2) 2003, 95-103.

Beta-cyclodextrin complexes of various flavonoids (hesperetin, hesperidin, naringenin, naringin) are characterised in R. Ficarra, S. Tommasini et al.; J. Pharm. Biomed. Analysis 29(6) 2002, 1005-1014.

R.-L. Wang, Yu Yang et al.; Yingyong Huaxue 19(7) 2002 702-704 compare the stability and solubility of various beta-cyclodextrin complexes of various flavonoids (rutin, quercetin, morin). Methyl-beta-cyclodextrin complexes proved to have particularly high solubility here.

K. Hostettmann, M. Lederer and A. Marston; Phytochemical Analysis 1186) 2000, 380-382 investigate the eluting action of 2-hydroxypropyl-beta-cyclodextrin on flavonoids absorbed on cellulose.

It has been found, in an unforeseeable manner for the person skilled in the art, that compositions for topical use comprising the above-mentioned complex compounds of the formula I or compounds of the formula II and cyclodextrins remedy the disadvantages of the prior art.

It is particularly advantageous here if the cyclodextrins used are γ-cyclodextrins, preferably gamma-cyclodextrins which are substituted by $C_{1-24}$-alkyl or $C_{1-24}$-hydroxyalkyl on one or more hydroxyl groups, such as, in particular, hydroxypropyl-γ-cyclodextrin, or mixtures of cyclodextrins which comprise at least 30% by weight, based on the total weight of the cyclodextrin mixture, of the above-mentioned γ-cyclodextrins.

It is furthermore advantageous for the content of cyclodextrins to be 0.01-20.0% by weight, preferably 0.05-10.0% by weight, particularly preferably 0.1-5.0% by weight, in each case based on the total weight of the composition. The proportion of the compounds of the formula II in the composition here is preferably 0.01 to 20% by weight, particularly preferably 0.05 to 10% by weight and especially preferably 0.1 to 5% by weight, based on the composition as a whole. The proportion of the compounds of the formula II in the composition is very particularly preferably 0.1 to 2% by weight, based on the composition as a whole.

The active-ingredient combinations in accordance with the invention or cosmetic or dermatological compositions comprising such active-ingredient combinations are satisfactory preparations in every respect. It was not foreseeable for the person skilled in the art that the compositions in accordance with the invention provide compounds of the formula I in increased bioavailability, maintain or restore the barrier properties of the skin better, counter drying-out of the skin better and protect the skin against environmental influences better than the compositions of the prior art.

On use of the complex compounds used in accordance with the invention or cosmetic or topical dermatological compositions having an active content of active-ingredient combinations used in accordance with the invention, effective treatment, but also prophylaxis, of deficient, sensitive or hypoactive skin states or deficient, sensitive or hypoactive states of skin appendages, of adverse changes in the skin and skin appendages caused by the environment (smoke, smog, reactive oxygen species, free radicals) and in particular light, of skin damage caused by light, of pruritus, of dry skin states and horny layer barrier defects, of inflammatory skin states and atopic eczema, seborrhoeic eczema, polymorphic light dermatosis, psoriasis, vitiligo, is surprisingly possible. However, the complex compounds according to the invention or cosmetic or topical, dermatological compositions having an effective content of complex compounds according to the invention also serve in a surprising manner for soothing sensitive or irritated skin,
for stimulation of intracellular DNA synthesis, in particular in the case of deficient or hypoactive skin states,
for increasing the skin's own protection and repair mechanisms (for example for dysfunctional enzymes, DNA, lipids, proteins),
for pre- and after-treatment in the case of topical use of laser and abrasive treatments which serve, for example, to reduce wrinkles and scars, in order to counter the resultant skin irritation and to promote the regeneration processes in the injured skin.

It is therefore also in accordance with the invention to use the complex compounds of the formula I or the compositions comprising the compounds of the formula II and cyclodextrins for the cosmetic or dermatological treatment or prophylaxis of undesired skin states,
for the prophylaxis and treatment of inflammatory skin states—also atopic eczema,
for skin protection in the case of dry skin determined to be sensitive,
for the protection of the skin against photoreactions,
for the treatment and prophylaxis of sensitive skin states,
for increasing the skin's own desoxidative protection,
and/or for improving the protection of the skin against environmental influences.

The complex compounds or compositions comprising the active-ingredient combination in accordance with the invention have a synergistic action in relation to the individual components in all these uses.

Advantageous in accordance with the invention is the use of cyclodextrins and/or cyclodextrin derivatives for increasing the solubility of compounds of the formula II. Furthermore advantageous is the use of cyclodextrins and/or cyclodextrin derivatives for improving the biological efficacy of compounds of the formula II.

In the flavonoid moieties of the compounds of the formula I or compounds of the formula II, the alkoxy groups are preferably linear and have 1 to 12 and preferably 1 to 8 C atoms. These groups thus conform to the formulae —O—$(CH_2)_m$—H, where m denotes 1, 2, 3, 4, 5, 6, 7 or 8 and in particular 1 to 5.

In the flavonoid moieties of the compounds of the formula I or compounds of the formula II, the hydroxyalkoxy groups are preferably linear and have 2 to 12 and preferably 2 to 8 C atoms. These groups thus conform to the formulae —O—$(CH_2)_n$—OH, where n denotes 2, 3, 4, 5, 6, 7 or 8, in particular 2 to 5 and especially preferably 2.

If one or more of the radicals $Z_1$ to $Z_4$ and $Z_6$ to $Z_{10}$ in the flavonoid moieties of the compounds of the formula I or compounds of the formula II denote a mono- or oligoglycoside radical, this glycoside radical is bonded directly to the corresponding benzene ring in the formula I via an oxygen atom. The mono- or oligoglycoside radicals are preferably built up from 1 to 3 glycoside units. These units are preferably selected from the group of the hexosyl radicals, in particular rhamnosyl radicals and glucosyl radicals. However, other hexosyl radicals, for example allosyl, altrosyl, galactosyl, gulosyl, idosyl, mannosyl and talosyl, may also advantageously be used. It may also be advantageous in accordance with the invention to use pentosyl radicals.

The mono- or oligoglycoside radicals present in the radical $Z_5$ of the flavonoid moieties of the compounds of the formula I or compounds of the formula II are bonded via an oxygen atom and are preferably built up from 1 to 3 glycoside units. The preferred units in the radicals $Z_1$ to $Z_4$ and $Z_6$ to $Z_{10}$ are also preferred for the mono- or oligoglycoside radical present in radical $Z_5$. The mono- or oligoglycoside radical present in the radical $Z_5$ is particularly preferably selected from the group consisting of the radicals of glucose, rhamnose and rutinose.

If X, $X_1$, $X_2$ and/or $X_3$ in the flavonoid moieties of the compounds of the formula I or compounds of the formula II denote a monoglycoside radical, these glycoside radicals are each bonded to the corresponding benzene ring via an oxygen atom. The preferred units in the radicals $Z_1$ to $Z_4$ and $Z_6$ to $Z_{10}$ are also preferred for this monoglycoside radical. If X, $X_1$, $X_2$ and/or $X_3$ denote a monoglycoside radical, the glucose radical is particularly preferred.

In a preferred embodiment of the invention, in particular if the water solubility of the flavonoid moieties of the compounds of the formula I or compounds of the formula II is to be increased, a polar group, for example, in each case independently of one another, a sulfate or phosphate group, is bonded to one or more hydroxyl groups of the radicals mentioned in the substituents $Z_1$ to $Z_{10}$. Suitable counterions are, for example, the ions of the alkali or alkaline earth metals, these being selected, for example, from sodium or potassium.

In a further preferred embodiment of the invention, preference is given to the flavonoid moieties of the compounds of the formula I or compounds of the formula II in which the radicals having an aromatic component which are present in the substituent $Z_5$ are bonded to the mono- or oligoglycoside radical likewise present in the radical $Z_5$ via an ester group —OOC—.

In a further preferred embodiment of the invention, subformulae of the formula I or formula II are derived from the compounds from the following group: rutin, trishydroxyethylrutin (troxerutin), isoquercetin, trishydroxy-ethylisoquercetin (troxeisoquercetin) and astragalin, and the sulfates and phosphates thereof.

In a further preferred embodiment, the flavonoid moieties of the compounds of the formula I or compounds of the formula II present in the compositions according to the invention are selected from the compounds of the formula IIA

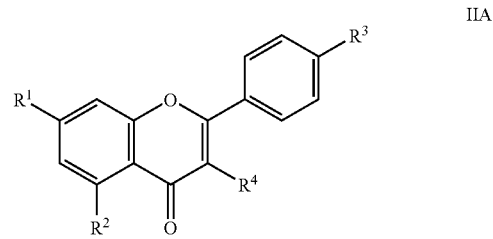

in which $R^1$, $R^2$ and $R^3$ each, independently of one another, denote OH, $CH_3COO$, an alkoxy radical having 1 to 8 C atoms or a monoglycoside radical, $R^4$ is a mono- or diglycoside radical, where bonded to the glycoside radical, in each case via an —O— group, is at least one group selected from

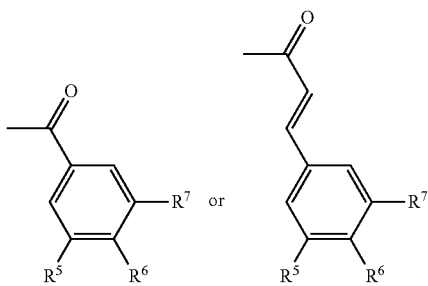
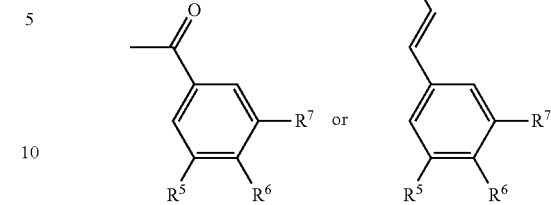

where $R^5$, $R^6$ and $R^7$ may each, independently of one another, be H or have the meaning of the radicals $R^1$ to $R^3$ and in which one or more hydrogen atoms in the OH groups of the glycoside radical(s) may each, independently of one another, also be replaced by acetyl or by $C_{1-24}$-alkyl radicals and where sulfate or phosphate may also each, independently of one another, be bonded to one or more hydroxyl groups of the compounds of the formula IIA.

In a preferred embodiment, the radical $R^2$ in the compounds of the formula IIA is selected from OH, $CH_3COO$ or an alkoxy radical having 1 to 8 C atoms.

In the compounds of the formula IIA, all OH groups of the mono- or diglycoside radical of $R^4$ may be esterified with a group of the formula Preferably, however, only one or two of the radicals derived from these radicals are bonded to the glycoside radical.

If $R^4$ is a mono- or diglycoside radical in which one or more hydrogen atoms of the OH groups have been replaced by acetyl or by alkyl radicals, all OH groups for which replacement is possible have then preferably been replaced by acetyl or by alkyl.

Of the alkoxy radicals having 1 to 8 C atoms mentioned in the compounds of the formula IIA, the methoxy group is preferred. Of the alkyl radicals having 1 to 8 C atoms mentioned in the compounds of the formula IIA, the methyl group is preferred.

The mono- and diglycoside radicals mentioned in the compounds of the formula IIA are preferably built up from glucose units.

Preferred compounds IIA1 to IIA13 selected from the compounds of the formula IIA are indicated below:

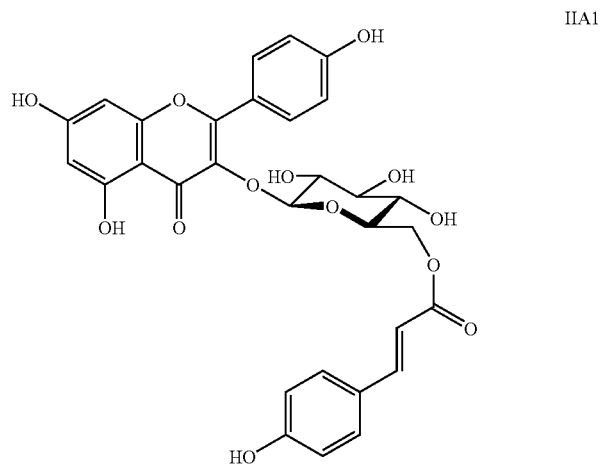

IIA1

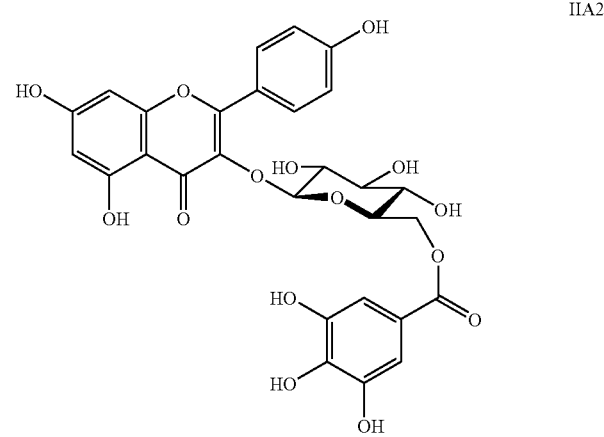

IIA2

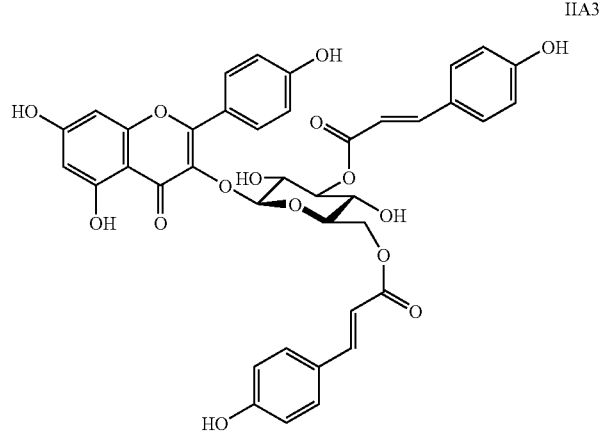

IIA3

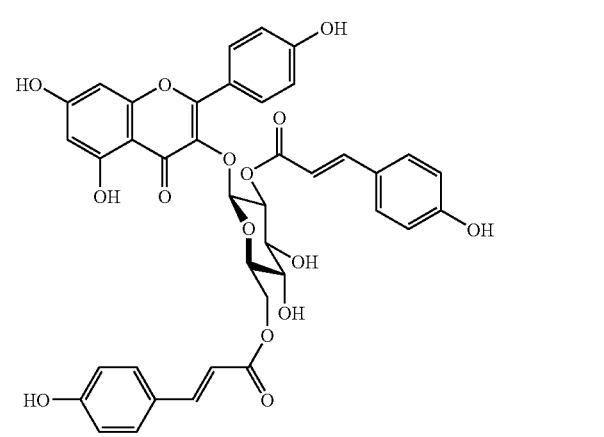

IIA4

-continued
IIA5
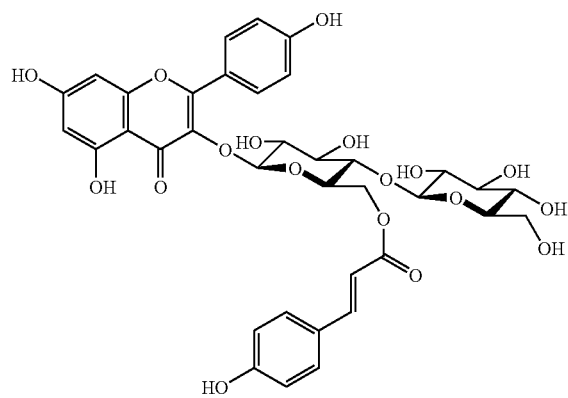
IIA6
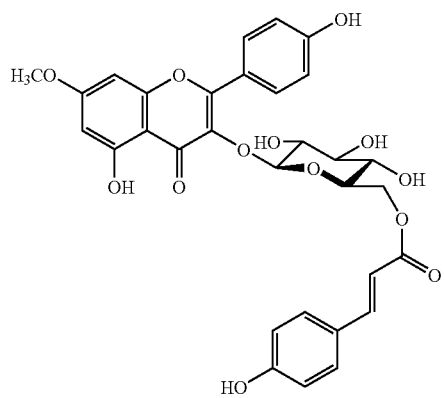
IIA7
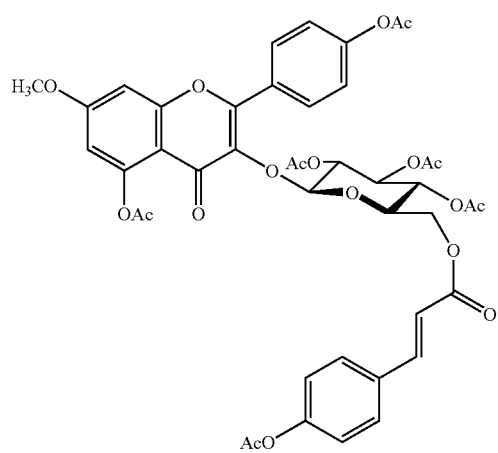
IIA8
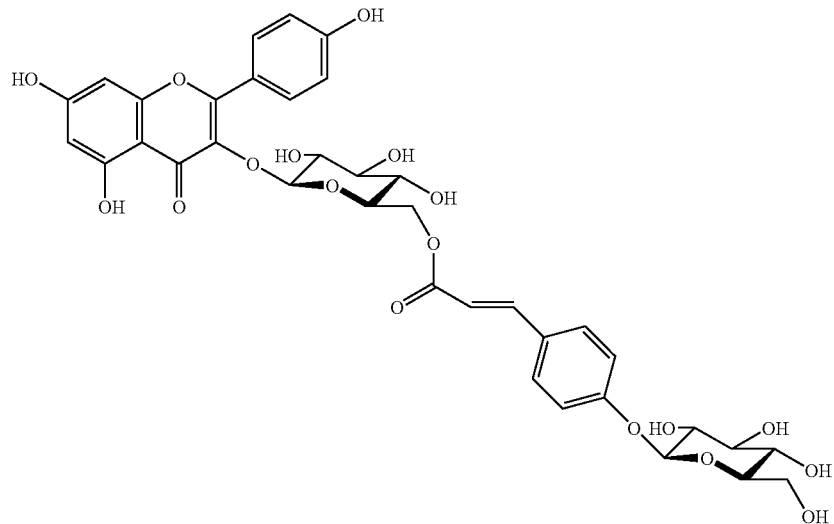

-continued
IIA9
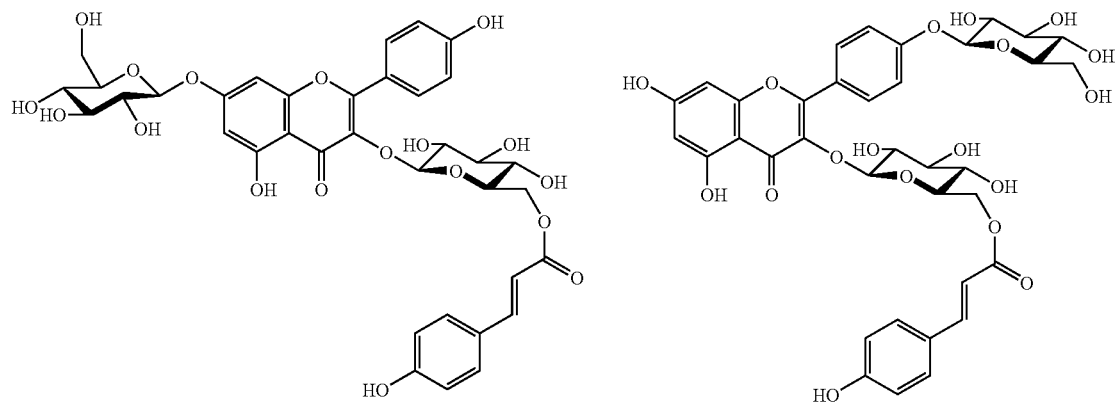
IIA10
IIA11
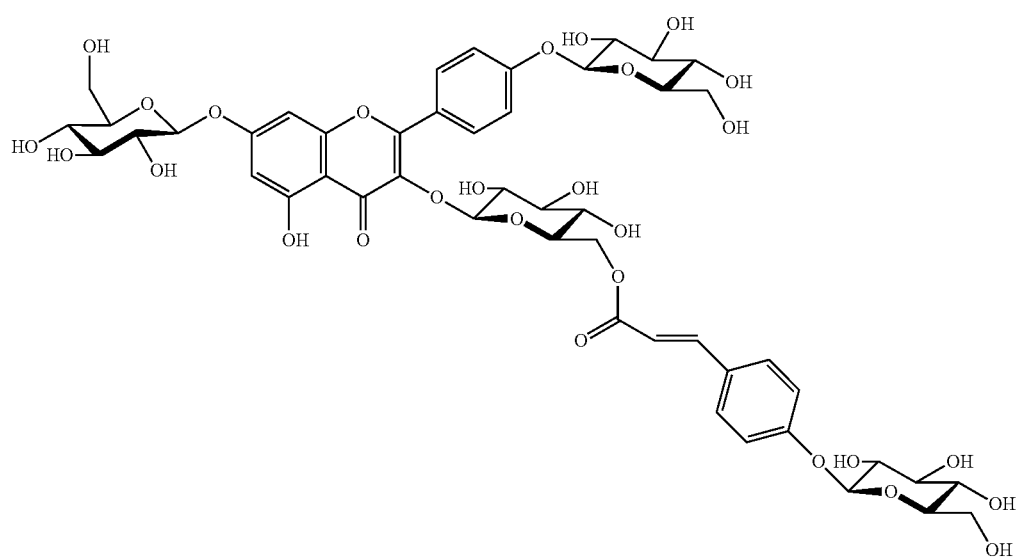
IIA12
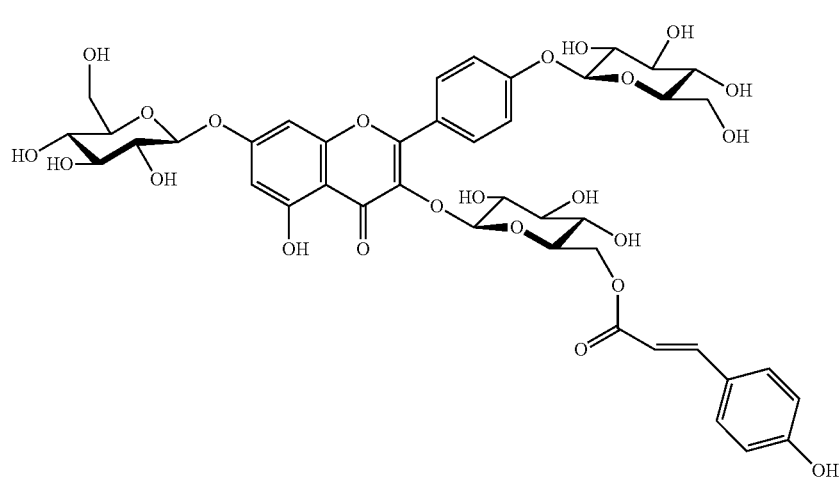

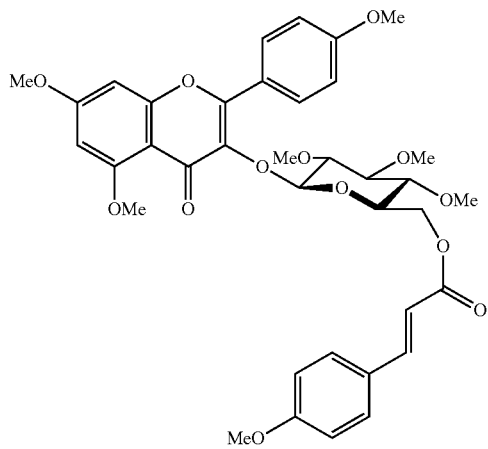

IIA13

In the compounds of the formulae IIA1 to IIA13 mentioned above, Me denotes methyl and Ac denotes acetyl.

Of the compounds of the formula IIA, particular preference is given to the compounds of the formulae IIA1 and IIA2. Very particular preference is given to the compound of the formula IIA1, i.e. tiliroside.

In a further preferred embodiment, the flavonoid moieties of the compounds of the formula I or compounds of the formula II present in the compositions according to the invention are selected from the compounds in which

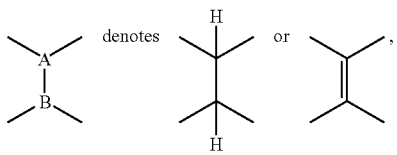

$Z_1$ to $Z_4$ and $Z_6$ to $Z_{10}$ each, independently of one another, denote H, OH, alkoxy, hydroxyalkoxy, mono- or oligoglycoside radicals and where the alkoxy and hydroxyalkoxy groups may be branched and unbranched and can have 1 to 18 C atoms, $Z_5$, n, m, k and M have the meanings given in claim 1, but the radicals X, $X_1$, $X_2$ and $X_3$ present in the substituent $Z_5$ each, independently of one another, denote OH, an alkoxy radical having 1 to 8 C atoms or a monoglycoside radical, and in which one or more hydrogen atoms in the OH groups of the glycoside radicals mentioned in the substituents $Z_1$ to $Z_{10}$ may each, independently of one another, also be replaced by $C_{1-24}$-alkyl radicals and where sulfate or phosphate may also each, independently of one another, be bonded to one or more hydroxyl groups of the radicals mentioned in the substituents $Z_1$ to $Z_{10}$.

In these flavonoid moieties of the compounds of the formula I or compounds of the formula II, $Z_1$ to $Z_4$ and $Z_6$ to $Z_{10}$ preferably each, independently of one another, denote H, OH, alkoxy or hydroxyalkoxy.

In a further preferred embodiment, the compounds of the formula IIA present in the compositions according to the invention are selected from the compounds in which $R^1$, $R^2$ and $R^3$ each, independently of one another, denote OH, an alkoxy radical having 1 to 8 C atoms or a monoglycoside radical, $R^4$ is a mono- or diglycoside radical, where bonded to the glycoside radical, in each case via an —O— group, is at least one group selected from

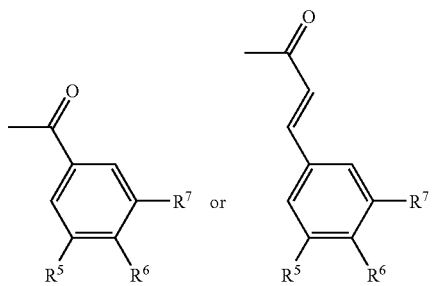

where $R^5$, $R^6$ and $R^7$ each, independently of one another, denote H, OH, an alkoxy radical having 1 to 8 C atoms or a monoglycoside radical, and in which one or more hydrogen atoms in the OH groups of the glycoside radical(s) may each, independently of one another, also be replaced by $C_{1-24}$-alkyl radicals and where sulfate or phosphate may also each, independently of one another, be bonded to one or more hydroxyl groups of the compounds of the formula IIA.

In these compounds of the formula IIA, $R^1$ to $R^3$ preferably each, independently of one another, denote OH or an alkoxy radical having 1 to 8 C atoms.

Some flavonoid moieties of the compounds of the formula I or compounds of the formula II, such as, for example, tiliroside, can be isolated from plants, for example from plants of the genus *Althaea, Aristolochia, Helianthemum, Lindera, Magnolia, Platanus, Potentilla, Quercus, Rosa, Sida, Sorbus* and/or *Tilia*. These compounds can be processed further either in isolated form or in unisolated form, i.e., for example, can be incorporated into compositions in the form of an extract or in the form of a purified extract or alternatively in the form of the pure substance prepared from the plant extract. Of the said genera, the following species are preferred: *Althaea officinalis, Althaea rosea, Aristolochia heterophylla, Helianthemum glomeratum, Lindera megaphylla, Magnolia salicifolia, Platanus acerifolia, Platanus occidentalis, Potentilla anserina, Quercus pubescens, Quercus suber, Quercus laurifolia, Quercus ilex, Quercus imbricaria, Quer-*

*cus virginiana, Rosa pomifera, Sida rhombifolia, Sida poeppigiana, Sida cordifolia, Sida glaziovii, Sorbus pendula, Tilia argenta* and *Tilia cordata*.

If the composition according to the invention comprises tiliroside, this compound, in a further preferred embodiment, has been used for the preparation of the composition in the form of a plant extract, a purified plant extract or in the form of the pure substance prepared from the plant extract.

In compositions of this type, the plant extract comprises, for example, 1 to 100% by weight of tiliroside. In one embodiment, the plant extract preferably comprises 5 to 90% by weight of tiliroside. In a further embodiment, the plant extract preferably comprises 30 to 100% by weight, particularly preferably 60 to 100% by weight and especially preferably 90 to 100% by weight of tiliroside.

In a further preferred embodiment, the plant extract has been isolated by extraction from the *Sida glaziovii* plant.

In all uses according to the invention in which tiliroside is used, tiliroside can be used, for example, in the form of a substance obtained synthetically, in the form of a plant extract, a purified plant extract or an individual substance or in the form of a pure substance isolated from the plant extract. In a preferred embodiment, tiliroside is used in the form of a plant extract, a purified plant extract or in the form of the pure substance prepared from the plant extract.

The flavonoid moieties of the compounds of the formula I or compounds of the formula II can be isolated or prepared by methods which are well known to the person skilled in the art and are described in the literature (for example in standard works, such as Houben-Weyl, Methodn der organischen Chemie [Methods of Organic Chemistry], Georg-Thieme-Verlag, Stuttgart).

For example, tiliroside occurs in plants and can be isolated by extraction. The plant extracts are prepared by conventional methods of extraction from the plants or plant parts. Suitable extraction methods may be: maceration, remaceration, digestion, agitation maceration, fluidised-bed extraction, ultrasound extraction, countercurrent extraction, percolation, repercolation, evacolation, diacolation or solid/liquid extraction with continuous reflux, which is carried out in a Soxhlet extractor.

The solvent used for the extraction can be, for example, water or an alcohol.

It can be ascribed to the general knowledge of the person skilled in the art how these extractions can be carried out in detail and the resultant crude extracts can be purified by generally conventional methods.

One possible synthetic route for tiliroside is, for example, also described in B. Vermes, H. Wagner, Stud. Org. Chem. (Amsterdam) (1982), Volume date 1981, 11 (Flavonoids, Bioflavonoids), 161-167 and in B. Vermes, V. M. Chari, H. Wagner, Helv. Chim. Acta (1981), 64(4), 1964-1967.

The synthesis of tiliroside is shown in scheme 1. 4',7-Dibenzylkaempferol (1) [H. Wagner, H. Danninger, O. Seligmann, M. Nógrádi, L. Farkas, N. Farnsworth, Chem. Ber. 103 (1978) 3768] is reacted with 2,3,4-tri-O-ace-tyl-6-O-chloroacetyl-β-D-glucopyranosyl bromide (2) in the presence of $Ag_2CO_3$ and pyridine to give compound 3. Compound 2 can be prepared by the method described in D. Y. Gagniere, P. J. A. Wottero, Carbohydrate Res. 28 (1973) 1965. Catalytic debenzylation and subsequent careful acetylation of compound 3 gives compound 4, from which compound 5 can be obtained after removal of the chloroacetyl group using thiourea. In this compound, only one hydroxyl group is free, meaning that the esterification of compound 5 can proceed selectively. The esterification using the acid chloride p-acetylcoumaroyl chloride 6 can be carried out in a mixture of pyridine and dichloromethane. An excess of acid chloride and a long reaction time (about 96 h) at room temperature is necessary to ensure that the esterification proceeds to completion. The final step, the selective saponification of the 7 acetyl groups in compound 7, can be carried out by the method described in G. Zemplén, Chem. Ber. 59 (1926) 1258. This is carried out using a catalytic amount of $NaOCH_3$ and a calculated amount of methanol.

Scheme 1

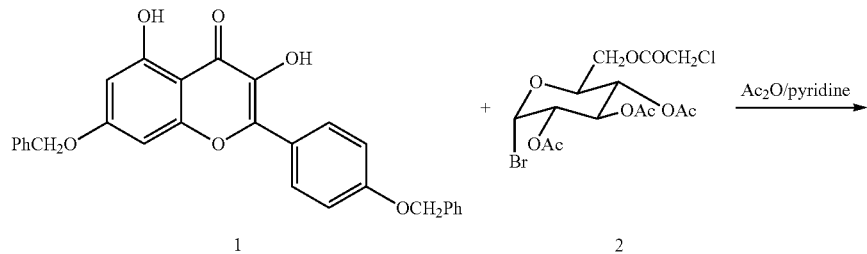

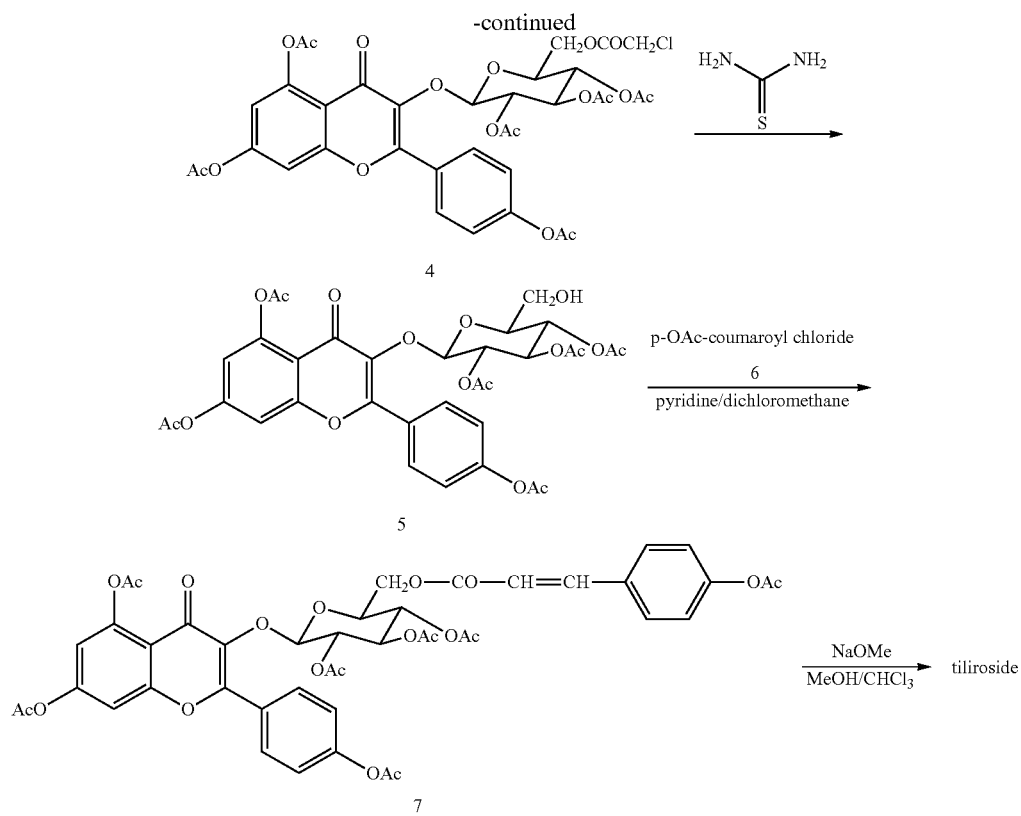

Ph = phenyl, Ac = CH₃CO, Me = methyl

Other flavonoid moieties of the compounds of the formula I or compounds of the formula II can be obtained by routine modification of the synthesis shown in scheme 1. Depending on the target molecule, different starting materials are used here, i.e. other optionally protected flavonoids, sugar components and radicals which are to be attached to the sugar component.

The esterification of glycosidic OH groups using aromatic sulfonic acid units can be carried out, for example, by the method described in A. B. Foster et al., J. Chem. Soc. (1954) 3625-3629. According to this method, the sugar component can, for example, be reacted with a corresponding aromatic sulfonyl chloride in pyridine.

The etherification of glycosidic OH groups using aromatic radicals can be carried out, for example, by the method described in P. Beraud et al., Tetrahedron Let. 30(3) (1989) 325-326. In this Mitsunobu reaction, the etherification is carried out, for example, by dissolving the sugar component in pyridine together with triphenylphosphine $PPh_3$ and reacting the solution with a corresponding phenol component and diethyl azodicarboxylate.

The etherification of glycosidic OH groups using radicals of saturated hydrocarbons can be carried out, for example, by the method described in M. Goebel et al., Tetrahedron 53(9) (1997) 3123-3134. The etherification is carried out, for example, by carefully adding sodium hydride to the sugar component in dry dimethylformamide under inert gas and then carefully reacting the mixture with a suitable alkylating reagent, such as, for example, a corresponding bromide.

The complex compounds of the formula I can be prepared by reacting compounds of the formula II with cyclodextrins in solution, preferably at elevated temperature. The present invention furthermore relates to a corresponding process.

It has been found that complexes comprising about 2 mol of cyclodextrin per mole of flavonoid of the formula II meet the requirements according to the invention in a particular manner. It is therefore preferred in accordance with the invention for o in formula I to be equal to 1 and p to be in the range from 1.75 to 2.1, preferably for p to be equal to 2.

Corresponding compounds can be prepared if the cyclodextrin is employed in excess or precisely in the molar ratio 2:1, based on the flavonoid.

In a preferred embodiment of the present invention, the composition is a composition for the protection of body cells against oxidative stress, in particular for reducing skin ageing, characterised in that it comprises one or more further antioxidants besides the one or more compounds of the formula I or of the formula II.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with compounds of the formula I or formula II in such compositions in ratios in the range from 1000:1 to 1:1000, preferably in amounts of 100:1 to 1:100.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. Vitamins are usually employed here with compounds of the formula I or formula II in ratios in the range from 1000:1 to 1:1000, preferably in amounts of 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers, I. M. C. M. Rietjens; Free Radical Biology & Medicine 2001, 31(7), 869-881, are investigating the pH dependence of the antioxidant action of hydroxyflavones. Quercetin exhibits the greatest activity amongst the structures investigated over the entire pH range.

Suitable antioxidants are furthermore compounds of the formula III

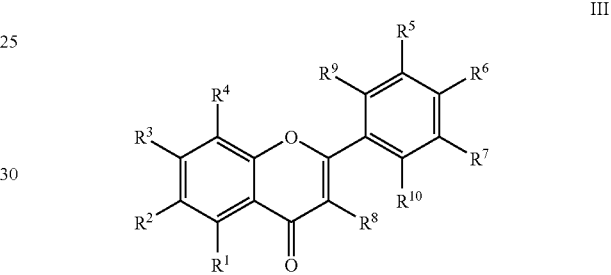

III where $R^1$ to $R^{10}$ may be identical or different and are selected from

H $OR^{11}$ straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3, where all $OR^{11}$, independently of one another, stand for

OH straight-chain or branched $C_1$- to $C_{20}$-alkoxy groups, straight-chain or branched $C_3$- to $C_{20}$-alkenyloxy groups, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or $C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or mono- and/or oligoglycosyl radicals, with the proviso that at least 4 radicals from $R^1$ to $R^7$ stand for OH and that at least 2 pairs of adjacent —OH groups are present in the molecule, or $R^2$, $R^5$ and $R^6$ stand for OH and the radicals $R^1$, $R^3$, $R^4$ and $R^{7-10}$ stand for H, as described in the earlier German patent application DE 10244282.7.

Compositions which are particularly preferred in accordance with the invention also comprise UV filters in addition to the compounds of the formula I or formula II.

On use of the dibenzoylmethane derivatives which are particularly preferred as UV-A filters in combination with the compounds of the formula I or formula II, an additional advantage arises: the UV-sensitive dibenzoylmethane derivatives are additionally stabilised by the presence of the compounds of the formula I or formula II. The present invention therefore furthermore relates to the use of the compounds of the formula I or formula II for the stabilization of dibenzoylmethane derivatives in compositions.

In principle, all UV filters are suitable for combination with the compounds of the formula I or formula II according to the invention. Particular preference is given to UV filters whose physiological acceptability has already been demonstrated. Both for UVA and UVB filters, there are many proven substances known from the specialist literature, for example benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyl-dibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292), isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;

and further substances, such as
2-ethylhexyl 2-cyano-3,3-diphenylacrylate (for example Eusolex® OCR),
3,3'-(1,4-phenylenedimethylene)bis(7,7-dimethyl-2-oxo-bicyclo[2.2.1]hept-1-ylmethanesulfonic acid and salts thereof (for example Mexoryl® SX) and
2,4,6-trianilino-(p-carbo-2'-ethylhexyl-1'-oxy)-1,3,5-triazine (for example Uvinul® T 150)
hexyl 2-(4-diethylamino-2-hydroxybenzoyl)benzoate (for example Uvinul®UVA Plus, BASF).

The compounds mentioned in the list should only be regarded as examples. It is of course also possible to use other UV filters.

These organic UV filters are generally incorporated into cosmetic formulations in an amount of 0.5 to 10 percent by weight, preferably 1-8%.

Further suitable organic UV filters are, for example,
2-(2H-benzotriazol-2-yl)-4-methyl-6-(2-methyl-3-(1,3,3,3-tetramethyl-1-(trimethylsilyloxy)disiloxanyl)propyl) phenol (for example Silatrizole®),
2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB),
α-(trimethylsilyl)-ω-[trimethylsilyl)oxy]poly[oxy(dimethyl [and approximately 6% of methyl[2-[p-[2,2-bis (ethoxycarbonyl)vinyl]phenoxy]-1-methyleneethyl] and approximately 1.5% of methyl[3-[p-[2,2-bis (ethoxycarbonyl)vinyl])phenoxy)propenyl) and 0.1 to 0.4% of (methylhydrogen]silylene]] (n≈60) (CAS No. 207 574-74-1)
2,2'-methylenebis(6-(2H-benzotriazol-2-yl)-4-(1,1,3,3-tetramethylbutyl)-phenol) (CAS No. 103 597-45-1)
2,2'-(1,4-phenylene)bis(1H-benzimidazole-4,6-disulfonic acid, mono-sodium salt) (CAS No. 180 898-37-7) and
2,4-bis{[4-(2-ethylhexyloxy)-2-hydroxy]phenyl}-6-(4-methoxyphenyl)-1,3,5-triazine (CAS No. 103 59745-, 187 393-00-6).
2-ethylhexyl 4,4'-[(6-[4-((1,1-dimethylethyl)aminocarbonyl)phenylamino]-1,3,5-triazine-2,4-diyl)diimino]bis (benzoate) (for example Uvasorb® HEB), Further suitable UV filters are also methoxyflavones corresponding to the earlier German patent application DE 10232595.2.

Organic UV filters are generally incorporated into cosmetic formulations in an amount of 0.5 to 20 percent by weight, preferably 1-15%.

Conceivable inorganic UV filters are those from the group of the titanium dioxides, such as, for example, coated titanium dioxide (for example Eusolex® T-2000, Eusolex® T-AQUA, Eusolex® T-AVO), zinc oxides (for example Sachtotec®), iron oxides or also cerium oxides. These inorganic UV filters are generally incorporated into cosmetic compositions in an amount of 0.5 to 20 percent by weight, preferably 2-10%.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and potassium, sodium and triethanolamine salts thereof.

The protective action against damaging effects of UV radiation can be optimised by combining one or more compounds of the formula I or formula II with further UV filters.

Optimised compositions may comprise, for example, the combination of the organic UV filters 4'-methoxy-6-hydroxyflavone with 1-(4-tert-butylphenyl)-3-(4-methoxyphenyl) propane-1,3-dione and 3-(4'-methylbenzylidene) -dl-camphor. This combination gives rise to broad-band protection, which can be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions according to the invention are preferably present in amounts which ensure that the encapsulated UV filters are present in the composition in the above-indicated amounts.

The compositions according to the invention may in addition comprise further conventional skin-protecting or skin-care active ingredients. These may in principle be any active ingredients known to the person skilled in the art.

These may be chromone derivatives. The term chromone derivatives here is preferably taken to mean certain chromen-2-one derivatives which are suitable as active ingredients for the preventive treatment of human skin and human hair against ageing processes and harmful environmental influences. At the same time, they exhibit a low irritation potential for the skin, have a positive effect on water binding in the skin, maintain or increase the elasticity of the skin and thus promote smoothing of the skin. These compounds preferably conform to the formula IV

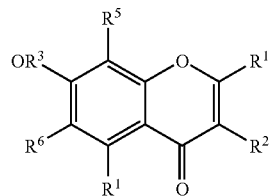

where $R^1$ and $R^2$ may be identical or different and are selected from H, —C(=O)—$R^7$, —C(=O)—$OR^7$,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3, $R^3$ stands for H or straight-chain or branched $C_1$- to $C_{20}$-alkyl groups, $R^4$ stands for H or $OR^8$, $R^5$ and $R^6$ may be identical or different and are selected from —H, —OH,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and $R^7$ stands for H, straight-chain or branched $C_1$- to $C_{20}$-alkyl groups, a polyhydroxyl compound, such as preferably an ascorbic acid radical or glycosidic radicals, and $R^8$ stands for H or straight-chain or branched $C_1$- to $C_{20}$-alkyl groups, where at least 2 of the substituents $R^1$, $R^2$, $R^4$-$R^6$ are not H or at least one substituent from $R^1$ and $R^2$ stands for —C(=O)—R or —C(=O)—$OR^7$.

The proportion of one or more compounds selected chromone derivatives in the composition according to the invention is preferably from 0.001 to 5% by weight, particularly preferably from 0.01 to 2% by weight, based on the composition as a whole.

It may furthermore be preferred for the composition according to the invention to comprise at least one repellent, where the repellent is preferably selected from N,N-diethyl-3-methylbenzamide, ethyl 3-(acetylbutylamino)-propionate, dimethyl phthalate, butopyronoxyl, 2,3,4,5-bis(2-butylene)-tetrahydro-2-furaldehyde, N,N-diethylcaprylamide, N,N-diethylbenzamide, o-chloro-N,N-diethylbenzamide, dimethyl carbate, di-n-propyl isocincho-meronate, 2-ethylhexane-1,3-diol, N-octylbicycloheptenedicarboximide, piperonyl butoxide, 1-(2-methylpropoxycarbonyl)-2-(hydroxyethyl)piperidine, or mixtures thereof, where it is particularly preferably selected from N,N-diethyl-3-methylbenzamide, ethyl 3-(acetylbutylamino)propionate 1-(2-methylpropoxycarbonyl)-2-(hydroxyethyl)piperidine, or mixtures thereof.

The compositions according to the invention which comprise repellents are preferably insect repellents. Insect repellents are available in the form of solutions, gels, sticks, rollers, pump sprays and aerosol sprays, with solutions and sprays forming the majority of the commercially available products.

The basis for these two product forms is usually formed by alcoholic or aqueous/alcoholic solutions with addition of fatting substances and slight perfuming.

Particularly preferred active ingredients are pyrimidinecarboxylic acids and/or aryl oximes.

Pyrimidinecarboxylic acids occur in halophilic microorganisms and play a role in osmoregulation of these organisms (E. A. Galinski et al., *Eur. J. Biochem.*, 149 (1985) page 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacterial cells. Pharmaceutical products, such as non-glycosylated, pharmaceutical active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European Patent Application EP-A-0 671 161 describes, in particular, that ectoine and hydroxyectoine are employed in cosmetic compositions, such as powders, soaps, surfactant-containing cleansing products, lipsticks, rouge, make-ups, care creams and sunscreen preparations.

Preference is given here to the use of a pyrimidinecarboxylic acid of the following formula V

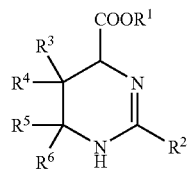

V in which $R^1$ is a radical H or C1-8-alkyl, $R^2$ is a radical H or C1-4-alkyl and $R^3$, $R^4$, $R^5$ and $R^6$ are each, independently of one another, a radical from the group H, OH, $NH_2$ and C1-4-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidine-carboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of 100:1 to 1:100 with respect to the compounds of the formula I, with ratios in the range 1:10 to 10:1 being particularly preferred.

Of the aryl oximes, preference is given to the use of 2-hydroxy-5-methyllaurophenone oxime, which is also known as HMLO, LPO or F5. Its suitability for use in cosmetic compositions is disclosed, for example, in DE-A41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which, in addition to the compound of the formula I, additionally comprise an aryl oxime, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

In a further, likewise preferred embodiment of the present invention, the composition according to the invention comprises at least one self-tanning agent.

Advantageous self-tanning agents which can be employed are, inter alia:

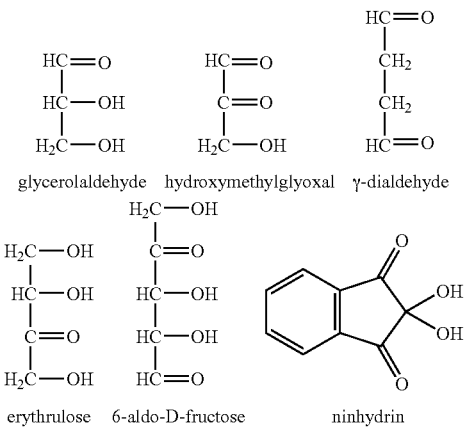

glycerolaldehyde  hydroxymethylglyoxal  γ-dialdehyde erythrulose  6-aldo-D-fructose  ninhydrin Mention should also be made of 5-hydroxy-1,4-naphthoquinone (juglone), which is extracted from the shells of fresh walnuts

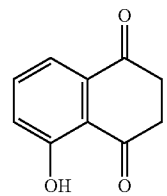

5-hydroxy-1,4-naphthoquinone (juglone)

and 2-hydroxy-1,4-naphthoquinone (lawsone), which occurs in henna leaves.

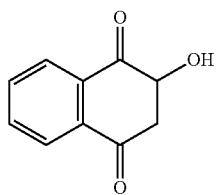

2-hydroxy-1,4-naphthoquinone (lawsone)

Very particular preference is given to 1,3-dihydroxyacetone (DHA), a tri-functional sugar which occurs in the human body, and derivatives thereof.

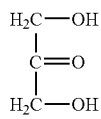

1,3-dihydroxyacetone (DHA)

Furthermore, the compositions according to the invention may also comprise dyes and coloured pigments. The dyes and coloured pigments can be selected from the corresponding positive list in the German Cosmetics Regulation or the EC list of cosmetic colorants. In most cases, they are identical with the dyes approved for foods. Advantageous coloured pigments are, for example, titanium dioxide, mica, iron oxides (for example $Fe_2O_3$, $Fe_3O_4$, $FeO(OH)$) and/or tin oxide. Advantageous dyes are, for example, carmine, Berlin Blue, Chromium Oxide Green, Ultramarine Blue and/or Manganese Violet. It is particularly advantageous to select the dyes and/or coloured pigments from the following list. The Colour Index numbers (CINs) are taken from the Rowe Colour Index, 3rd Edition, Society of Dyers and Colourists, Bradford, England, 1971.

| Chemical or other name | CIN | Colour |
|---|---|---|
| Pigment Green | 10006 | green |
| Acid Green 1 | 10020 | Green |
| 2,4-Dinitrohydroxynaphthalene-7-sulfonic acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-Dihydroxyazobenzene | 11920 | Orange |
| Solvent Red 3 | 12010 | Red |
| 1-(2'-Chloro-4'-nitro-1'-phenylazo)-2-hydroxynaphthalene | 12085 | Red |
| Pigment Red 3 | 12120 | Red |
| Ceres Red; Sudan Red; Fat Red G | 12150 | Red |
| Pigment Red 112 | 12370 | Red |
| Pigment Red 7 | 12420 | Red |
| Pigment Brown 1 | 12480 | Brown |
| 4-(2'-Methoxy-5'sulfonyldiethylamide-1'-phenylazo)-3-hydroxy-5''-chloro-2'',4''-dimethoxy2-naphthanilide | 12490 | Red |
| Disperse Yellow 16 | 12700 | Yellow |
| 1-(4-Sulfo-1-phenylazo)-4-aminobenzene-5-sulfonic acid | 13015 | Yellow |
| 2,4-Dihydroxyazobenzene-4'-sulfonic acid | 14270 | Orange |
| 2-(2,4-Dimethylphenylazo-5-sulfonyl)-1-hydroxynaphthalene-4-sulfonic acid | 14700 | Red |
| 2-(4-Sulfo-1-naphthylazo)-1-naphthol-4-sulfonic acid | 14720 | Red |
| 2-(6-Sulfo-2,4-xylylazo)-1-naphthol-5-sulfonic acid | 14815 | Red |
| 1-(4'-Sulfophenylazo)-2-hydroxynaphthalene | 15510 | Orange |
| 1-(2-Sulfonyl-4-chloro-5-carboxy-1-phenylazo)-2-hydroxynaphthalene | 15525 | Red |

-continued

| Chemical or other name | CIN | Colour |
|---|---|---|
| 1-(3-Methylphenylazo-4-sulfonyl)-2-hydroxynaphthalene | 15580 | Red |
| 1-(4',(8')-Sulfonylnaphthylazo)-2-hydroxynaphthalene | 15620 | Red |
| 2-Hydroxy-1,2'-azonaphthalene-1'-sulfonic acid | 15630 | Red |
| 3-Hydroxy-4-phenylazo-2-naphthylcarboxylic acid | 15800 | Red |
| 1-(2-Sulfo-4-methyl-1-phenylazo)-2-naphthylcarboxylic acid | 15850 | Red |
| 1-(2-Sulfo-4-methyl-5-chloro-1-phenylazo)-2-hydroxynaphthalene-3-carboxylic acid | 15865 | Red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | Orange |
| 1-(4-Sulfo-1-phenylazo)-2-naphthol-6-sulfonic acid | 15985 | Yellow |
| Allura Red | 16035 | Red |
| 1-(4-Sulfo-1-naphthylazo)-2-naphthol-3,6-disulfonic acid | 16185 | Red |
| Acid Orange 10 | 16230 | Orange |
| 1-(4-Sulfo-1-naphthylazo)-2-naphthol-6,8-disulfonic acid | 16255 | Red |
| 1-(4-Sulfo-1-naphthylazo)-2-naphthol-3,6,8-trisulfonic acid | 16290 | Red |
| 8-Amino-2-phenylazo-1-naphthol-3,6-disulfonic acid | 17200 | Red |
| Acid Red 1 | 18050 | Red |
| Acid Red 155 | 18130 | Red |
| Acid Yellow 121 | 18690 | Yellow |
| Acid Red 180 | 18736 | Red |
| Acid Yellow 11 | 18820 | Yellow |
| Acid Yellow 17 | 18965 | Yellow |
| 4-(4-Sulfo-1-phenylazo)-1-(4-sulfophenyl)-5-hydroxy-pyrazolone-3-carboxylic acid | 19140 | Yellow |
| Pigment Yellow 16 | 20040 | Yellow |
| 2,6-(4'-Sulfo-2'',4''-dimethyl)bisphenylazo)1,3-dihydroxy-benzene | 20170 | Orange |
| Acid Black 1 | 20470 | Black |
| Pigment Yellow 13 | 21100 | Yellow |
| Pigment Yellow 83 | 21108 | Yellow |
| Solvent Yellow | 21230 | Yellow |
| Acid Red 163 | 24790 | Red |
| Acid Red 73 | 27290 | Red |
| 2-[4'-(4''-Sulfo-1'''-phenylazo)-7'-sulfo-1'-naphthylazo]-1-hydroxy-7-aminonaphthalene-3,6-disulfonic acid | 27755 | black |
| 4-[4''-Sulfo-1'''-phenylazo)-7'-sulfo-1'-naphthylazo]-1-hydroxy-8-acetylaminonaphthalene-3,5-disulfonic acid | 28440 | Black |
| Direct Orange 34, 39, 44, 46, 60 | 40215 | Orange |
| Food Yellow | 40800 | Orange |
| trans-β-Apo-8'-carotene aldehyde ($C_{30}$) | 40820 | Orange |
| trans-Apo-8'-carotinic acid ($C_{30}$) ethyl ester | 40850 | Orange |
| Canthaxanthine | 40850 | Orange |
| Acid Blue 1 | 42045 | Blue |
| 2,4-Disulfo-5-hydroxy-4'-4''-bis(diethylamino)triphenylcarbinol | 42051 | Blue |
| 4-[(-4-N-Ethyl-p-sulfobenzylamino)phenyl-(4-hydroxy-2-sulfophenyl)(methylene)-1-(N-ethylN-p-sulfobenzyl)-2,5-cyclohexadienimine] | 42053 | Green |
| Acid Blue 7 | 42080 | Blue |
| (N-Ethyl-p-sulfobenzylamino)phenyl-(2-sulfophenyl)-methylene-(N-ethyl-N-p-sulfobenzyl)Δ$^{2,5}$-cyclohexadienimine | 42090 | Blue |
| Acid Green 9 | 42100 | Green |
| Diethyldisulfobenzyldi-4-amino-2-chlorodi-2-methylfuchsonimmonium | 42170 | Green |
| Basic Violet 14 | 42510 | Violet |
| Basic Violet 2 | 42520 | Violet |
| 2'-Methyl-4'-(N-ethyl-N-m-sulfobenzyl)amino-4''-(N-diethyl)-amino-2-methyl-N-ethylN-m-sulfobenzylfuchsonimmonium | 42735 | Blue |
| 4'-(N-Dimethyl)amino-4''-(N-phenyl)aminonaphtho-N-dimethylfuchsonimmonium | 44045 | Blue |
| 2-Hydroxy-3,6-disulfo-4,4'-bisdimethylaminonaphtho-fuchsonimmonium | 44090 | Green |
| Acid Red 52 | 45100 | Red |
| 3-(2'-Methylphenylamino)-6-(2'-methyl-4'-sulfophenylamino)-9-(2''-carboxyphenyl)xanthenium salt | 45190 | Violet |
| Acid Red 50 | 45220 | Red |
| Phenyl-2-oxyfluorone-2-carboxylic acid | 45350 | yellow |
| 4,5-Dibromofluorescein | 45370 | Orange |
| 2,4,5,7-Tetrabromofluorescein | 45380 | Red |

-continued

| Chemical or other name | CIN | Colour |
|---|---|---|
| Solvent Dye | 45396 | Orange |
| Acid Red 98 | 45405 | Red |
| 3',4',5',6'-Tetrachloro-2,4,5,7-tetrabromofluorescein | 45410 | Red |
| 4,5-Diiodofluorescein | 45425 | Red |
| 2,4,5,7-Tetraiodofluorescein | 45430 | Red |
| Quinophthalone | 47000 | Yellow |
| Quinophthalonedisulfonic acid | 47005 | Yellow |
| Acid Violet 50 | 50325 | Violet |
| Acid Black 2 | 50420 | Black |
| Pigment Violet 23 | 51319 | Violet |
| 1,2-Dioxyanthraquinone, calcium/aluminium complex | 58000 | Red |
| 3-Oxypyrene-5,8,10-sulfonic acid | 59040 | Green |
| 1-Hydroxy-4-N-phenylaminoanthraquinone | 60724 | Violet |
| 1-Hydroxy-4-(4'-methylphenylamino)anthraquinone | 60725 | Violet |
| Acid Violet 23 | 60730 | Violet |
| 1,4-Di(4'-methylphenylamino)anthraquinone | 61565 | Green |
| 1,4-Bis(o-sulfo-p-toluidino)anthraquinone | 61570 | Green |
| Acid Blue 80 | 61585 | Blue |
| Acid Blue 62 | 62045 | Blue |
| N,N'-Dihydro-1,2,1',2'-anthraquinonazine | 69800 | Blue |
| Vat Blue 6; Pigment Blue 64 | 69825 | Blue |
| Vat Orange 7 | 71105 | orange |
| Indigo | 73000 | Blue |
| Indigodisulfonic acid | 73015 | Blue |
| 4,4'-Dimethyl-6,6'-dichlorothioindigo | 73360 | Red |
| 5,5'Dichloro-7,7'-dimethylthioindigo | 73385 | violet |
| Quinacridone Violet 19 | 73900 | violet |
| Pigment Red 122 | 73915 | Red |
| Pigment Blue 16 | 74100 | blue |
| Phthalocyanines | 74160 | blue |
| Direct Blue 86 | 74180 | blue |
| Chlorinated phthalocyanines | 74260 | green |
| Natural Yellow 6, 19; Natural Red 1 | 75100 | yellow |
| Bixin, Nor-Bixin | 75120 | orange |
| Lycopene | 75125 | yellow |
| trans-alpha-, -beta- or -gamma-Carotene | 75130 | orange |
| Keto and/or hydroxyl derivatives of carotene | 75135 | yellow |
| Guanine or pearlescent agent | 75170 | white |
| 1,7-Bis(4-hydroxy-3-methoxyphenyl)1,6-heptadiene-3,5-dione | 75300 | yellow |
| Complex salt (Na, Al, Ca) of carminic acid | 75470 | Red |
| Chlorophyll a and b; copper compounds of chlorophylls and chlorophyllines | 75810 | green |
| Aluminium | 77000 | white |
| Aluminium hydroxide | 77002 | white |
| Water-containing aluminium silicates | 77004 | white |
| Ultramarine | 77007 | blue |
| Pigment Red 101 and 102 | 77015 | Red |
| Barium sulfate | 77120 | white |
| Bismuth oxychloride and mixtures thereof with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromium oxide | 77288 | green |
| Chromium oxide, water-containing | 77278 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide hydrate | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and mixtures thereof with mica | 77891 | white |
| Zinc oxide | 77947 | white |
| 6,7-Dimethyl-9-(1'-D-ribityl)isoalloxazine, lactoflavin | | yellow |
| Sugar dye | | brown |
| Capsanthin, capsorubin | | orange |
| Betanin | | red |
| Benzopyrylium salts, anthocyans | | red |
| Aluminium, zinc, magnesium and calcium stearate | | white |
| Bromothymol Blue | | blue |

It may furthermore be favourable to select, as dye, one or more substances from the following group: 2,4-dihydroxyazobenzene, 1-(2'-chloro-4'-nitro-1'phenylazo)-2-hydroxynaphthalene, Ceres Red, 2-(4-sulfo-1-naphthylazo)-1-naphthol-4-sulfonic acid, the calcium salt of 2-hydroxy-1,2'-azonaphthalene-1'-sulfonic acid, the calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-naphthylazo)-2-naphthol-3,6-disulfonic acid, 1-(4-sulfo-1-naphthylazo)-2-naphthol-6,8-disulfonic acid, the aluminium salt of 4-(4-sulfo-1-phenylazo)-2-(4-sulfophenyl)-5-hydroxypyrazolone-3-carboxylic acid, the aluminium and zirconium salts of 4,5-dibromofluorescein, the aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium salt of indigodisulfonic acid, red and black iron oxide (CIN: 77 491 (red) and 77 499 (black)), iron oxide hydrate (CIN: 77492), manganese ammonium diphosphate and titanium dioxide.

Also advantageous are oil-soluble natural dyes, such as, for example, paprika extract, β-carotene or cochineal.

Also advantageous for the purposes of the present invention are gel creams comprising pearlescent pigments. Particular preference is given to the types of pearlescent pigment listed below:

1. Natural pearlescent pigments, such as, for example,
    1. "pearl essence" (guanine/hypoxanthine mixed crystals from fish scales) and
    2. "mother-of-pearl" (ground mussel shells)
2. Monocrystalline pearlescent pigments, such as, for example, bismuth oxychloride (BiOCl)
3. Layered substrate pigments: for example mica/metal oxide The basis for pearlescent pigments is formed by, for example, pulverulent pigments or castor oil dispersions of bismuth oxychloride and/or titanium dioxide as well as bismuth oxychloride and/or titanium dioxide on mica. The lustre pigment listed under CIN 77163, for example, is particularly advantageous.

Also advantageous are, for example, the following pearlescent pigment types based on mica/metal oxide:

| Group | Coating/layer thickness | Colour |
|---|---|---|
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Coloured lustre pigments | $Fe_2O_3$ | bronze |
| | $Fe_2O_3$ | copper |
| | $Fe_2O_3$ | red |
| | $Fe_2O_3$ | red-violet |

| Group | Coating/layer thickness | Colour |
|---|---|---|
| Combination pigments | $Fe_2O_3$ | red-green |
| | $Fe_2O_3$ | black |
| | $TiO_2/Fe_2O_3$ | gold shades |
| | $TiO_2/Cr_2O_3$ | green |
| | $TiO_2$/Berlin Blue | dark blue |

Particular preference is given to, for example, the pearlescent pigments available from Merck under the trade names Timiron, Colorona or Dichrona.

The list of the said pearlescent pigments is of course not intended to be limiting. Pearlescent pigments which are advantageous for the purposes of the present invention can be obtained by numerous routes known per se. For example, other substrates apart from mica can also be coated with further metal oxides, such as, for example, silica and the like. For example, $TiO_2$- and $Fe_2O_3$-coated $SiO_2$ particles ("Ronasphere" grades), which are marketed by Merck and are particularly suitable for the optical reduction of fine wrinkles, are advantageous.

It may additionally be advantageous to completely omit a substrate such as mica. Particular preference is given to pearlescent pigments prepared using $SiO_2$. Such pigments, which may additionally also have goniochromatic effects, are available, for example, from BASF under the trade name Sicopearl Fantastico.

It may also be advantageous to employ Engelhard/Mearl pigments based on calcium sodium borosilicate coated with titanium dioxide. These are available under the name Reflecks. Due to their particle size of 40-80 μm, they have a glitter effect in addition to the colour.

Also particularly advantageous are effect pigments available from Flora Tech under the trade name Metasomes Standard/Glitter in various colours (yellow, red, green, blue). The glitter particles here are in the form of mixtures with various assistants and dyes (such as, for example, the dyes with the Colour Index (CI) numbers 19140, 77007, 77289, 77491).

The dyes and pigments can be in individual form or in the form of a mixture and mutually coated with one another, with different colour effects generally being caused by different coating thicknesses. The total amount of dyes and colouring pigments is advantageously selected from the range from, for example, 0.1% by weight to 30% by weight, preferably 0.5 to 15% by weight, in particular 1.0 to 10% by weight, in each case based on the total weight of the compositions.

All compounds or components which can be used in the compositions are either known and commercially available or can be synthesised by known processes.

The one or more compounds of the formula I can be incorporated into cosmetic or dermatological compositions in the customary manner. Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower compositions. Any desired customary excipients, auxiliaries and, if desired, further active ingredients may be added to the composition.

Preferred auxiliaries originate from the group of the preservatives, antioxidants, stabilisers, solubilisers, vitamins, colorants, odour improvers.

Ointments, pastes, creams and gels may comprise the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary excipients, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary excipients, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary excipients, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary excipients, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary excipients, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary excipients, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye-shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:
  mineral oils, mineral waxes;
  oils, such as triglycerides of capric or caprylic acid, furthermore natural oils, such as, for example, castor oil;
  fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and wax, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyidodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate, of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984 or 5984, in each case individually or in combination.

In particular, mixture of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

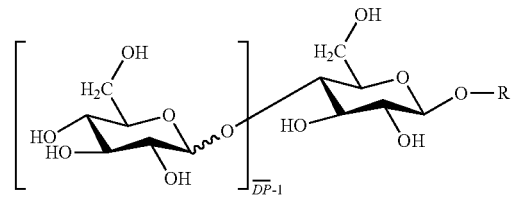

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- . . . i-fold glucosylated products in percent by weight. Advantageous in accordance with the invention is the selection of products having degrees of glucosylation of 1-2, particularly advantageously of 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used in accordance with the invention are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and auxiliaries or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group of the substances which are distinguished by the structural formula

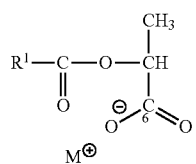

where $R^1$ denotes a branched or unbranched alkyl radical having 1 to 30 carbon atoms, and $M^+$ is selected from the group of the alkali metal ions and the group of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the substances which are distinguished by the structural formula

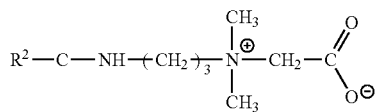

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14)

cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate, An ethoxylated alkyl ether carboxylic acid or salt thereof which can be used is advantageously sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate(cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:
fatty alcohols having 8 to 30 C atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

The preferred compositions in accordance with the invention are particularly suitable for protecting human skin against ageing processes and against oxidative stress, i.e. against damage caused by free radicals, as are produced, for example, by solar irradiation, heat or other influences. In this connection, it is in the various administration forms usually used for this application. For example, it may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) of the formula I or formula II, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) of the formula I or formula II, the composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that at least one compound of the formula I or formula II having radicals as described above is mixed with a cosmetically or dermatologically or food-suitable excipient, and to the use of a compound of the formula I or formula II for the preparation of a composition.

The compositions according to the invention can be prepared using techniques which are well known to the person skilled in the art.

The mixing can result in dissolution, emulsification or dispersion of the compound of the formula I or formula II in the excipient.

It has also been noted that compounds of the formula I or formula II can have a stabilising effect on the composition. When used in corresponding products, the latter thus also remain stable for longer and do not change their appearance. In particular, the effectiveness of the ingredients, for example vitamins, is retained even in the case of application over extended periods or extended storage. This is, inter alia, particularly advantageous in the case of compositions for protecting the skin against the effect of UV rays since these cosmetics are exposed to particularly high stresses by UV radiation.

The positive effects of compounds of the formula I or formula II give rise to their particular suitability for use in cosmetic or pharmaceutical compositions.

The properties of compounds of the formula I or formula II should likewise be regarded as positive for use in foods or as food supplements or as functional food. The further explanations given for foods also apply correspondingly to food supplements and functional food.

The foods which can be enriched with one or more compounds of the formula I or formula II in accordance with the present invention include all materials which are suitable for consumption by animals or consumption by humans, for example vitamins and provitamins thereof, fats, minerals or amino acids. (The foods may be solid, but also liquid, i.e. in the form of a beverage).

The present invention accordingly furthermore relates to the use of a compound of the formula I or formula II as food additive for human or animal nutrition, and to compositions which are foods or food supplements and comprise corresponding excipients.

Foods which can be enriched with one or more compounds of the formula I or formula II in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I or formula II in accordance with the present invention are corn or cereals from a single plant species and materials produced from plant species of this type, such as, for example, cereal syrup, rye flour, wheat flour or oat bran. Mixtures of foods of this type are also suitable for being enriched with one or more compounds of the formula I or formula II in accordance with the present invention, for example multivitamin preparations, mineral mixtures or sweetened juice. As further examples of foods which can be enriched with one or more compounds of the formula I or formula II in accordance with the present invention, mention may be made of food compositions, for example prepared cereals, biscuits, mixed drinks, foods prepared especially for children, such as yoghurt, diet foods, low-calorie foods or animal feeds.

The foods which can be enriched with one or more compounds of the formula I or formula II in accordance with the present invention thus include all edible combinations of carbohydrates, lipids, proteins, inorganic elements, trace elements, vitamins, water or active metabolites of plants and animals.

The foods which can be enriched with one or more compounds of the formula I or formula II in accordance with the present invention are preferably administered orally, for example in the form of meals, pills, tablets, capsules, powders, syrup, solutions or suspensions.

The foods according to the invention enriched with one or more compounds of the formula I or formula II can be prepared using techniques which are well known to the person skilled in the art.

Due to their action, compounds of the formula I or formula II are also suitable as medicament ingredient Compounds of the formula I or formula II can be used, for example, for the preventative treatment of inflammation and allergies of the skin and in certain cases for preventing certain types of cancer. Compounds of the formula I or formula II are particularly suitable for the preparation of a medicament for the treatment of inflammation, allergies and irritation, in particular of the skin. It is furthermore possible to prepare medicaments which act as vein tonic, as cuperose inhibitor, as chemical, physical or actinic erythema inhibitor, as agent for the treatment of sensitive skin, as decongestant, as desiccant, as slimming agent, as anti-wrinkle agent, as stimulators for the synthesis of components of the extracellular matrix, as strengthening agent for improving skin elasticity, and as anti-ageing agent. Furthermore, compounds of the formula I or formula II which are preferred in this connection exhibit antiallergic and anti-inflammatory and antiirritative actions. They are therefore suitable for the preparation of medicaments for the treatment of inflammation or allergic reactions.

Preferred inflammation-inhibiting compositions may comprise at least one additional inflammation-inhibiting active ingredient, which is preferably selected from the glucocorticoids or tacrolimus.

Tacrolimus has been isolated from the fungus *Streptomyces tsukukaensis* and exhibits an immunosuppressive action.

Suitable glucocorticoids are, for example, prednisone, cloprednol, triamcinolone, methylprednisolone, dexamethasone, betamethasone, desoximetasone, clobetasone butyrate, halcinonide, clobetasol propionate, prednisolone, hydrocortisone butyrate, betamethasone dipropionate, fluocinolone acetonide, fluocinolone acetonide, betamethasone valerate, hydrocortisone (cortisol), cortisone acetate, prednicarbate diflucortolone valerate, triamcinolone acetonide, fluocinolone acetonide, fluocortolone and fluocortolone 21-hexanoate.

Compositions of this type which comprise an active-ingredient combination of at least one complex compound of the formula I or at least one compound of the formula II and at least one cyclodextrin with at least one of the above-indicated further inflammation-inhibiting active ingredients exhibit a particularly strong inflammation-inhibiting action.

In particular, it has been found that the complex compounds of the formula I and the compositions according to the invention can be employed particularly advantageously in the treatment of atopic eczema, such as, in particular, milk crust, neurodermatitis, prurigo and dermatitis sicca.

It has been found here that they
are able greatly to reduce the acute symptoms,
are able to reduce the frequency of occurrence of acute symptoms,
in general contribute to an improvement in the skin picture.

The compositions comprising one or more compounds of the formula I are also suitable for the protection of human skin or for the protection of body cells against oxidative stress, i.e., for example, against damage by free radicals, as generated, for example, by sunlight, heat or other influences.

The compositions comprising one or more compounds of the formula I are particularly suitable for reducing skin ageing.

The present invention thus also relates to the use of one or more compounds of the formula I as active ingredient for protection against oxidative stress. The present invention furthermore relates to the use of one or more compounds of the formula I for preventing skin ageing.

The compounds of the formula I have antiallergic, antiinflammatory, inflammation-inhibiting and antiirritative properties and can thus be used for the treatment or preventative treatment of allergies, inflammation and irritation, in particular of the skin. The present invention therefore furthermore relates to the use of one or more compounds of the formula I as active ingredient having an antiallergic, antiinflammatory, inflammation-inhibiting and antiirritative action.

Uses preferred in accordance with the invention of the compounds of the formula I or of compositions comprising at least one compound of the formula I here are, in particular, the use for prophylaxis against time- and/or light-induced ageing processes of the human skin or human hair, in particular for prophylaxis against dry skin, wrinkling and/or pigment defects, and/or for reducing or preventing damaging effects of UV rays on the skin, and for prophylaxis against or reduction of skin unevenness, such as wrinkles, fine lines, rough skin or large-pored skin.

If the compounds to be employed in accordance with the invention have free hydroxyl groups, they additionally exhibit, in addition to the properties described, an action as antioxidant and/or free-radical scavenger. Preference is therefore also given to compositions having light-protection properties comprising at least one compound of the formula I which is characterised in that at least one of the radicals $R^1$ to $R^3$ stands for OH, where preferably at least one of the radicals $R^1$ and $R^2$ stands for OH.

In order that the compounds of the formula I are able to develop their positive action as free-radical scavengers on the skin particularly well, it may be preferred to allow the compounds of the formula I to penetrate into deeper skin layers. Several possibilities are available for this purpose. Firstly, the compounds of the formula I can have an adequate lipophilicity in order to be able to penetrate through the outer skin layer into epidermal layers. As a further possibility, corresponding transport agents, for example liposomes, which enable transport of the compounds of the formula I through the outer skin layers may also be provided in the composition. Finally, systemic transport of the compounds of the formula I is also conceivable. The composition is then designed, for example, in such a way that it is suitable for oral administration.

In general, the substances of the formula I act as free-radical scavengers. Free radicals of this type are not generated only by sunlight, but instead are formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leucocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

It is assumed that the preferred compounds of the formula I also act as enzyme inhibitors. They presumably inhibit histidine decarboxylase, protein kinases, elastase, aldose reductase and hyaluronidase, and therefore enable the intactness of the basic substance of vascular sheaths to be maintained. Furthermore, they presumably inhibit non-specifically catechol O-methyl transferase, causing the amount of available catecholamines and thus the vascular strength to be increased. Furthermore, they inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. All these uses and the use of the compounds of the formula I for the preparation of compositions which can be employed correspondingly are expressly also a subject-matter of the present invention.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris. verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, for the treatment of skin problems caused by UV radiation.

Furthermore, compounds of the formula I have only a weak inherent colour. The weak inherent colour is, for example, a major advantage if an inherent colour of the ingredients is undesired in the products for aesthetic reasons.

The proportion of the compounds of the formula I in the composition is preferably 0.01 to 20% by weight, particularly preferably 0.05 to 10% by weight and especially preferably 0.1 to 5% by weight, based on the composition as a whole. The proportion of the compounds of the formula I in the composition is very particularly preferably 0.1 to 2% by weight, based on the composition as a whole.

Even without further comments, it is assumed that a person skilled in the art will be able to utilise the above description in the broadest scope. The preferred embodiments should therefore merely be regarded as descriptive disclosure which is absolutely not limiting in any way. The complete disclosure content of all applications and publications mentioned above and below is incorporated into this application by way of reference. The following examples are intended to illustrate the present invention. However, they should in no way be regarded as limiting. All compounds or components which can be used in the compositions are either known and commercially available or can be synthesised by known methods. The INCI names of the raw materials used are as follows:

EXAMPLES

List of Raw Materials Employed

| Raw material | INCI name |
| --- | --- |
| Abil WE 09 | Polyglyceryl 4-Isostearate, Cetyl Dimethicone Copolyol, Hexyl Laurate |
| Antaron V-220 | PVP/Eicosene Copolymer |
| Arlacel 80 | Sorbitan Oleate |
| Arlacel 165 V | Glyceryl Stearate, PEG-100 Stearate |
| Avocado oil | Persea Gratissima |
| Beeswax | Beeswax |
| Biobase ™ EP | Glyceryl Stearate, Cetearyl Alcohol, Sodium Stearoyl Lactylate, Lecithin |
| Carbopol ETD 2050 | Carbomer |
| Cetiol V | Decyl Oleate |
| Cetyl alcohol | Cetyl Alcohol |
| Cetyl isononanoate | Cetyl Isononanoate |
| Cutina HR | Hydrogenated Castor Oil |
| Dimeticon | Dimethicone |
| Eusolex ® 232 | Phenylbenzimidazole Sulfonic Acid |
| Eusolex ® 2292 | Octyl Methoxycinnamate, BHT |
| Eusolex ® 6300 | 4-Methylbenzylidene Camphor |
| Eusolex 8300 | 4-Methylbenzylidene |
| Eusolex ® 9020 | Butyl Methoxydibenzoylmethane |
| Eusolex ® HMS | Homosalate |
| Eusolex T-Aqua | Aqua (Water), Titanium Dioxide, Alumina, Sodium Metaphosphate, Phenoxyethanol, Sodium Methylparaben |
| Eutanol G | Octyldodecanol |
| Germaben II | Propylene Glycol, Diazolidinyl Urea, Methylparaben, Propylparaben |
| Germaben II-E | Propylene Glycol, Diazolidinyl Urea, Methylparaben, Propylparaben |
| Glycerin | Glycerin |
| Glycerin (87%) | Glycerin |
| Glycerin (87% extra pure) | Glycerin |
| Glycerin, anhydrous | Glycerin |
| Hetester PHA | Propylene Glycol Isoceteth-3 Acetate |
| Hexyl laurate | Hexyl Laurate |
| Imwitor 960 K flakes | Glyceryl Stearate SE |
| Isolan PDI | Diisostearoyl Polyglyceryl 3-Diisostearate |
| Isopropyl myristate | Isopropyl Myristate |
| Isopropyl palmitate | Isopropyl Palmitate |
| Jojoba oil | Buxus Chinensis (Jojoba Oil) |
| Karion F liquid | Sorbitol |
| Keltrol RD | Xanthan Gum |
| Magnesium sulfate | Magnesium Sulfate |
| Magnesium sulfate heptahydrate | Magnesium Sulfate |
| Methyl 4-hydroxybenzoate | Methylparaben |
| Miglyol 812 | Caprylic/Capric Triglyceride |
| Miglyol 812 N | Caprylic/Capric Triglyceride |
| Miglyol 812, neutral oil | Caprylic/Capric Triglyceride |
| Mirasil CM5 | Cyclomethicone |
| Mirasil DM 350 | Dimethicone |
| Montanov 68 | Cetearyl Alcohol, Cetearyl Glucoside |
| Sodium chloride | Sodium Chloride |
| Sodium hydroxide solution, 10% | Sodium Hydroxide |
| Oxynex ® K | PEG-8, Tocopherol, Ascorbyl Palmitate, Ascorbic Acid, Citric Acid |
| Panthenol-D | Panthenol |
| Paracera M | Microwax |
| Paraffin oil, liquid | Mineral Oil |
| Perfume oil TND-2417 | Perfume |
| Pemulen TR-1 | Acrylates/$C_{10-30}$ Alkyl Acrylate Crosspolymer |
| Pemulen ® TR-2 | Acrylates/$C_{10-30}$ Alkyl Acrylate Crosspolymer |
| Performa ® V 825 | Synthetic Wax |
| Polyglyceryl 2-dipolyhydroxystearate | Polyglyceryl-2 Dipolyhydroxystearate |
| Prisorine 2021 | Isopropyl Isostearate |
| 1,2-Propanediol | Propylene Glycol |
| Propyl 4-hydroxybenzoate | Propylparaben |
| Rhodicare S | Xanthan Gum |
| RonaCare ™ ASC III | Aqua, Lecithin, Dipalmitoyl Hydroxyproline, Phenoxyethanol, Tall Oil Sterol, Linoleic Acid, Tocopherol, Sodium Ascorbate, Mannitol, Methylparaben, Ethylparaben, Propylparaben, Butylparaben |
| RonaCare ™ Bisabolol | Bisabolol |
| RonaCare ™ Ectoine | Ectoine |
| RonaCare ™ LPO | Lauryl p-Cresol Ketoxime |
| RonaCare ™ Tocopherol acetate | Tocopheryl Acetate |

| Raw material | INCI name |
| --- | --- |
| Sepigel 305 | Polyacrylamide, $C_{13-14}$ Isoparaffin, Laureth-7 |
| SFE 839 | Cyclopentasiloxane, Dimethicone/ Vinyldimethicone Crosspolymer |
| Shea butter | Shea Butter |
| Steareth-2 | Steareth-2 |
| Steareth-10 | Steareth-10 |
| Stearic acid | Stearic Acid |
| DL-α-tocopherol acetate | Tocopherol Acetate |
| Triethanolamine | Triethanolamine |
| Triethanolamine extra pure | Triethanolamine |
| Water, demineralised | Aqua (Water) |
| Zinc stearate | Zinc Stearate |

Example A

Preparation of a Tiliroside/Cyclodextrin Complex 0.9 g of hydroxypropyl-gamma-cyclodextrin (Aldrich; 2'-hydroxypropyl-cyclooctaamylose; Cas. No. 128446-34-4) are initially introduced in 8 ml of water and warmed to 50° C. 0.15 g of tiliroside are dissolved in 8 ml of ethanol at room temperature and added dropwise to the initially introduced solution. The solution is stirred at 50° C. for three days. The ethanol is distilled off from the solution. The residue is evaporated to dryness under reduced pressure, and the yellow solid which remains is post-dried at 40° C. and 200 mbar overnight. Yield: 1.02 g=97.2% of theory of yellow crystal-line residue.

Characterisation:

Evidence of Complex Formation by Means of 2D-NMR Spectrum

ROESY spectra show interaction of spatially adjacent atoms. Spatially close atoms give signals in the ROESY 2D-NMR spectrum. Here, the complex was measured by means of ROESY in order to clarify the molecular constituents of the tiliroside via which the complex formation takes place.

In the ROESY spectrum (solvent $D_2O$), signals occur which can be assigned to an interaction of the tiliroside atoms 2''', 3''', 6 and 8 (cf. formula drawing) with the cyclodextrin molecules.

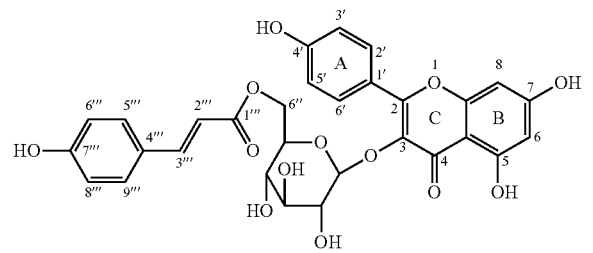

The NMR data fit the interpretation that a complex has been formed which consists of tiliroside and two cyclodextrin molecules which are spatially arranged on the aromatic ring of the coumaric acid or on ring B of the flavone basic structure.

Tiliroside Content in the Solid (HPLC Determination)

8.0 mg of tiliroside are dissolved in 3 ml of methanol and 1 ml of THF and made up to 10.0 ml with eluent (acetonitrile/ $H_2O$ 2/8) in a volumetric flask. (peak area of 12783970).

11.5 mg of complex are dissolved in 3 ml of methanol and 1 ml of tetra-hydrofuran and made up to 10.0 ml with eluent (acetonitrile/$H_2O$ 2/8) in a volumetric flask. (peak area of tiliroside 2503977).

Calculation: 8.0 mg of tiliroside give an area of 12783970

11.5 mg of tiliroside would give an area of 18376957.

An area of 2503977 is found.

Consequently: the complex consists of 13.6% by weight of tiliroside. A tiliroside:cyclodextrin weight ratio of 13.6:86.4 is present in the complex. This corresponds to a molar ratio of 1:2 (theoretical weight ratio of the tiliroside (cyclodextrin)$_2$ complex=14.4:85.6).

The complex compound is a [tiliroside] [hydroxypropyl-gamma-cyclodextrin]$_2$ complex.

Solubility of the Tiliroside/Cyclodextrin Complex:

0.5 g of complex is dissolved in 1 ml of water without reaching saturation. This corresponds to a solubility, based on pure tiliroside, of at least 72 mg/ml.

In the following example formulations 1 to 5, tiliroside is in each case employed as tiliroside/hydroxypropyl-gamma-cyclodextrin complex in accordance with Example A.

Example 1

Lotion (W/O) for application to the skin

| | | % by wt. |
| --- | --- | --- |
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| | Tiliroside | 0.5 |
| B | Glycerol | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:
0.05% of propyl 4-hydroxybenzoate
0.15% of methyl 4-hydroxybenzoate

Example 2

Lotion (W/O) for application to the skin

| | | % by wt. |
| --- | --- | --- |
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| B | Sulfated tiliroside, sodium salt (Example A) | 1.0 |
| | Glycerol | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:
0.05% of propyl 4-hydroxybenzoate
0.15% of methyl 4-hydroxybenzoate Example 3

| | Lotion (W/O) for application to the skin | |
|---|---|---|
| | | % by wt. |
| A | 4,6,3',4'-Tetrahydroxybenzylcoumaranone-3 | 1.0 |
| | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| | Tiliroside | 1.0 |
| B | Glycerol | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:
0.05% of propyl 4-hydroxybenzoate
0.15% of methyl 4-hydroxybenzoate Example 4

A cream (O/W) comprising ectoine is prepared from the following components:

| | | | % by wt. |
|---|---|---|---|
| A | Paraffin, liquid | (1) | 8.0 |
| | Isopropyl myristate | (1) | 4.0 |
| | Mirasil CM5 | (2) | 3.0 |
| | Stearic acid | (1) | 3.0 |
| | Arlacel 165 V | (3) | 5.0 |
| | Tiliroside | | 1.0 |
| B | Glycerol (87%) | (1) | 3.0 |
| | Germaben II | (4) | 0.5 |
| | Water, demineralised | | to 100 |
| C | RonaCare ™ ectoine | (1) | 1.0 |

Preparation

Firstly, phases A and B are warmed separately to 75° C. Phase A is then slowly added to phase B with stirring and stirred until a homogeneous mixture has formed. After homogenisation of the emulsion, the mixture is cooled to 30° C. with stirring. The mixture is subsequently warmed to 35° C., phase C is added, and the mixture is stirred until homogeneous.

Sources of Supply

| (1) | Merck KGaA |
| (2) | Rhodia |
| (3) | Uniqema |
| (4) | ISP |

Example 5

| | Topical composition as W/O emulsion | | |
|---|---|---|---|
| | | | % by wt. |
| A | Isolan PDI | (2) | 3.0 |
| | Paraffin oil, liquid | (1) | 17.0 |
| | Isopropyl myristate | | 5.0 |
| | Beeswax | | 0.2 |
| | Cutina HR | (2) | 0.3 |
| | Tiliroside | | 1.0 |
| B | Water, demineralised | | to 100 |
| | Glycerol (87%) | | 4.0 |
| | Magnesium sulfate | | 1.0 |
| | Germaben II-E | (3) | 1.0 |
| C | RonaCare ™ LPO | (1) | 2.0 |

Preparation

Phases A and B are warmed to 75° C. Phase B is added to phase A with stirring. The mixture is subsequently homogenised at 9000 rpm for 2 min. using the Turrax. The resultant mixture is cooled to 30 to 35° C., and C is stirred in.

Sources of Supply

| (1) | Merck KGaA |
| (2) | Goldschmidt AG |
| (3) | ISP |

Example 6

Compositions

Formulations of cosmetic compositions which comprise the tiliroside/2-hydroxypropyl-gamma-cyclodextrin complex (=tiliroside/CD) in accordance with Examples A are indicated by way of example below. In addition, the INCI names of the commercially available compounds are indicated.

UV-Pearl, OMC stands for the composition having the INCI name: Water (for EU: Aqua), Ethylhexyl Methoxycinnamate, Silica, PVP, Chlorphenesin, BHT; this composition is commercially available from Merck KGaA, Darmstadt, under the name Eusolex®UV Pearl™OMC. The other UV-Pearls indicated in the tables each have an analogous composition, with OMC being replaced by the UV filters indicated.

TABLE 1

| W/O emulsions (numbers in % by weight) | | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Titanium dioxide | | 2 | 5 | | | | | | | 3 |
| Tiliroside/CD | 5 | 3 | 2 | 1 | 2 | 1 | 2 | 1 | 1 | 1 |
| Zinc oxide | | | | | | | | 5 | 2 | |
| UV-Pearl, OMC | 30 | 15 | 15 | 15 | 15 | 15 | 15 | 15 | 15 | 15 |
| Polyglyceryl-3 Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium dioxide | 3 | | 2 | | 3 | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| Tiliroside/CD | 1 | 3 | 2 | 5 | 1 | 3 | 7 | 2 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerol | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium dioxide | | 2 | 5 | | | | | | | 3 | 3 |
| Benzylidene malonate polysiloxane | | | | 1 | | | | | 1 | 1 | |
| Zinc oxide | | | | | | | | 5 | 2 | | |
| Tiliroside/CD | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |
| BMDBM | | | | | | | | | | | 2 |
| UV-Pearl OMC, 4-Methylbenzylidene Camphor | 25 | | | | | | | | | | |
| Polyglyceryl-3-Dimerate | 3 | 3 | 3 | 3 | 3 | 3 | 3 | 3 | 3 | 3 | 3 |

TABLE 1-continued

| W/O emulsions (numbers in % by weight) | | | | | | | | | | | |
|---|---|---|---|---|---|---|---|---|---|---|---|
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

| O/W emulsions, numbers in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium dioxide | | 2 | 5 | | | | | | | 3 |
| Methylene Bis-Benztriazolyl Tetramethylbutylphenol | | | | | | 1 | 2 | 1 | | |
| 2-(1-Ethylhexyl)-5,7-dihydroxy-chromen-4-one | | | | 1 | 2 | | | | 1 | 1 |
| 4'-Methoxy-6-hydroxyflavone | 1 | 3 | | 2 | | 5 | | 5 | 2 | |
| Tiliroside/CD | 5 | 5 | 5 | 5 | 5 | 5 | 5 | 5 | 5 | 5 |
| 2-Carboxyl-5,7-dihydroxy-chromen-4-one | 1 | 5 | 4 | | 6 | | 7 | | 2 | 1 |
| 4-Methylbenzylidene Camphor | 2 | | 3 | | 4 | | 3 | | 2 | |
| BMDBM | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Trometamine | | | 1.8 | | | | | | | |
| Glycerol | | | | | | | | | | |
| Water | to 100 | to 100 | to 100 | to 100 | to 100 | to 100 | to 100 | to 100 | to 100 | to 100 |

| | 2-11 | 2-12 | 2-13 | 2-14 | 2-15 | 2-16 | 2-17 | 2-18 |
|---|---|---|---|---|---|---|---|---|
| Titanium dioxide | 3 | | 2 | | | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| 4'-Methoxy-7-β-glucosidylflavone | | | | 1 | 2 | | | |
| Tiliroside/CD | 1 | 3 | 0.1 | 2 | 0.5 | 5 | 0.2 | 5 |
| 2-Carboxyl-7-hydroxy-chromen-4-one | 5 | 5 | 5 | 5 | 5 | 5 | 5 | 5 |
| Ectoin | 1 | 5 | 4 | | 6 | | 7 | |
| Zinc oxide | | | 2 | | | | | |
| UV-Pearl, OMC | 15 | 15 | 15 | 30 | 30 | 30 | 15 | 15 |
| 4-Methylbenzylidene Camphor | | | | 3 | | | | |
| BMDBM | | | | 1 | | | | |
| Phenylbenzimidazole Sulfonic Acid | | | | | 4 | | | |
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |

TABLE 2-continued

| O/W emulsions, numbers in % by weight | | | | | | | | |
|---|---|---|---|---|---|---|---|---|
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| Persea Gratissima | | | | | 8 | 8 | 8 | 8 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Tromethamine | | | | | 1.8 | | | |
| Glycerol | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | | | | | | | 3 | 3 | | 2 |
| Benzylidene malonate polysiloxane | 1 | 2 | | | 1 | 1 | | 1 | 0.5 | |
| 7,8,3',4'-Tetrahydroxyflavone | | | | 1 | 2 | | | | 1 | 1 |
| Tiliroside/CD | 1 | 3 | 0.2 | 2 | 0.3 | 5 | 0.5 | 5 | 2 | 0.8 |
| 2-Methyl-5,7-dihydroxy-chromen-4-one | 5 | 5 | 5 | 5 | 5 | 5 | 5 | 5 | 5 | 5 |
| Methylene Bis-Benztriazolyl Tetramethylbutylphenol | | 1 | 2 | 1 | | | | 1 | 1 | 0.5 |
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Glycerol | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

| Gels, numbers in % by weight | | | | | | | | | | |
|---|---|---|---|---|---|---|---|---|---|---|
| a = aqueous gel | 3-1 | 3-2 | 3-3 | 3-4 | 3-5 | 3-6 | 3-7 | 3-8 | 3-9 | 3-10 |
| Titanium dioxide | | 2 | 5 | | | | | | | 3 |
| Tiliroside/CD | 1 | 3 | 0.2 | 2 | 0.5 | 5 | 1 | 5 | 2 | 1.5 |
| Benzylidene malonate polysiloxane | | | | 1 | 1 | 2 | | | 1 | 1 |
| Methylene Bis-Benztriazolyl Tetramethylbutylphenol | | 1 | | | | | 1 | 2 | 1 | |
| Zinc oxide | | | | 2 | | | | 5 | 2 | |
| UV-Pearl, Ethylhexyl Methoxycinnamate | 30 | 15 | 15 | 15 | 15 | 15 | 15 | 15 | 15 | 15 |
| 4-Methylbenzylidene Camphor | | | | | 2 | | | | | |
| Butylmethoxydibenzoylmethane | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

The invention claimed is:
1. A complex compound of the following formula

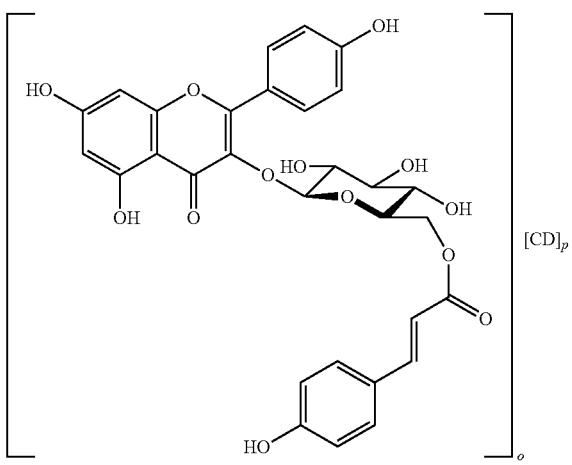

wherein
CD is a gamma-cyclodextrin,
o is 1, and
p is 2.

2. A complex compound according to claim 1, wherein the gamma-cyclodextrin is $C_{1-24}$-alkyl- or $C_{1-24}$-hydroxyalkyl-substituted on one or more hydroxyl groups.

3. A complex compound according to claim 1, wherein the gamma-cyclodextrin is hydroxypropyl-gamma-cyclodextrin.

4. A composition comprising a complex compound of claim 1 and an excipient.

5. A composition according to claim 4, which comprises one or more antioxidants and/or one or more UV filters.

6. A composition according to claim 4, which comprises one or more further active ingredients having a skin-care and/or inflammation-inhibiting action.

7. A composition according to claim 4, which further comprises one or more glucocorticoids or tacrolimus.

8. A method for the therapy of eczema, comprising administering to a subject in need thereof a complex compound according to claim.

9. A method according to claim 8, wherein the eczema is atopic eczema, milk crust, neurodermatitis, prurigo or dermatitis sicca.

10. A method for the care, preservation or improvement of the general state of the skin or hair, comprising administering to a subject in need thereof a complex compound according to claim 1.

11. A process for preparing a complex compound according to claim 1, comprising reacting a compound of formula IIA1

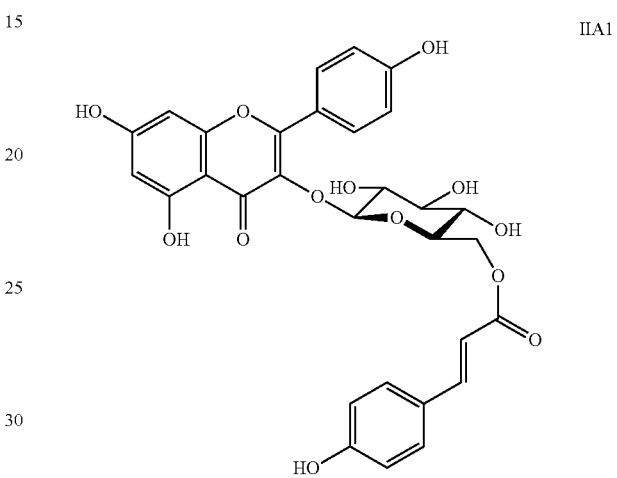

with CD, which is a gamma-cyclodextrin, in a solution.

12. A process according to claim 11, wherein the gamma-cyclodextrin is hydroxypropyl-gamma-cyclodextrin.

13. A process for preparing a composition according to claim 4, comprising mixing the complex compound with an excipient.

* * * * *

UNITED STATES PATENT AND TRADEMARK OFFICE
CERTIFICATE OF CORRECTION

PATENT NO. : 7,960,430 B2  Page 1 of 1
APPLICATION NO. : 10/586458
DATED : June 14, 2011
INVENTOR(S) : Corinna Wirth et al.

It is certified that error appears in the above-identified patent and that said Letters Patent is hereby corrected as shown below:

Column 62, line 3 reads: "according to claim." Should read --according to claim 1.--.

Signed and Sealed this
Twelfth Day of June, 2012

David J. Kappos
*Director of the United States Patent and Trademark Office*